United States Patent
Blanquart

(10) Patent No.: US 10,750,933 B2
(45) Date of Patent: *Aug. 25, 2020

(54) MINIMIZE IMAGE SENSOR I/O AND CONDUCTOR COUNTS IN ENDOSCOPE APPLICATIONS

(71) Applicant: Depuy Synthes Products, Inc., Raynham, MA (US)

(72) Inventor: Laurent Blanquart, Westlake Village, CA (US)

(73) Assignee: DePuy Synthes Products, Inc., Raynham, MA (US)

(\*) Notice: Subject to any disclaimer, the term of this patent is extended or adjusted under 35 U.S.C. 154(b) by 1049 days.

This patent is subject to a terminal disclaimer.

(21) Appl. No.: 14/214,794

(22) Filed: Mar. 15, 2014

(65) Prior Publication Data

US 2014/0275783 A1    Sep. 18, 2014

Related U.S. Application Data

(60) Provisional application No. 61/791,547, filed on Mar. 15, 2013, provisional application No. 61/790,590, filed on Mar. 15, 2013.

(51) Int. Cl.
*A61B 1/04* (2006.01)
*A61B 1/00* (2006.01)
(Continued)

(52) U.S. Cl.
CPC ...... *A61B 1/00124* (2013.01); *A61B 1/00006* (2013.01); *A61B 1/00018* (2013.01); *A61B 1/00055* (2013.01); *A61B 1/00066* (2013.01); *A61B 1/051* (2013.01); *A61B 1/053* (2013.01); *H04N 5/23203* (2013.01); *H04N 5/3532* (2013.01); *H04N 13/239* (2018.05); *H04N 2005/2255* (2013.01)

(58) Field of Classification Search
CPC .......... H04N 5/2628; H01L 2924/0002; H01L 27/14601; H01L 27/14603; H01L 27/14609; H01L 27/14643; H01L 2924/00
USPC ......................................................... 348/68
See application file for complete search history.

(56) References Cited

U.S. PATENT DOCUMENTS 3,796,220 A    3/1974  Bredemeier
3,858,577 A    1/1975  Bass et al.
(Continued)

FOREIGN PATENT DOCUMENTS

AU    2012253261       6/2016
AU    2012253253 B2    1/2017
(Continued)

OTHER PUBLICATIONS

H.Kurino et al., Intelligent image sensor chip with three dimensional structure, Technical Digest, International Electron Devices Meeting 1999, Dec. 5, 1999, pp. 879-882.

*Primary Examiner* — Masum Billah
(74) *Attorney, Agent, or Firm* — Terrence J. Edwards; TechLaw Ventures, PLLC

(57) ABSTRACT

The disclosure extends to systems and methods for reducing the area of an image sensor by employing bi-directional pads used for both image data issuance and configuration command reception and internal supply voltage generation, for reducing the number of conductors in an endoscope system.

33 Claims, 12 Drawing Sheets

(51) Int. Cl.
  *A61B 1/05* (2006.01)
  *H04N 5/232* (2006.01)
  *H04N 13/239* (2018.01)
  *H04N 5/353* (2011.01)
  *H04N 5/225* (2006.01)

(56) References Cited

U.S. PATENT DOCUMENTS

| | | |
|---|---|---|
| 4,011,403 A | 3/1977 | Epstein et al. |
| 4,153,356 A | 5/1979 | Hama |
| 4,350,150 A | 9/1982 | Kubota et al. |
| 4,363,963 A | 12/1982 | Ando |
| 4,429,686 A | 2/1984 | Hosoda |
| 4,433,675 A | 2/1984 | Konoshima |
| 4,436,095 A | 3/1984 | Kruger |
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkle et al. |
| 4,740,837 A | 4/1988 | Yanagisawa et al. |
| 4,741,327 A | 5/1988 | Yabe |
| 4,745,471 A | 5/1988 | Takamura et al. |
| 4,773,396 A | 9/1988 | Okazaki |
| 4,786,965 A | 11/1988 | Yabe |
| 4,800,424 A | 1/1989 | Noguchi |
| 4,831,444 A | 5/1989 | Kato |
| 4,832,003 A | 5/1989 | Yabe |
| 4,845,555 A | 7/1989 | Yabe et al. |
| 4,853,772 A | 8/1989 | Kikuchi |
| 4,866,526 A | 9/1989 | Ams et al. |
| 4,888,639 A | 12/1989 | Yabe et al. |
| 4,918,521 A | 4/1990 | Yabe et al. |
| 4,938,205 A | 7/1990 | Nudelman |
| 4,942,473 A | 7/1990 | Zeevi et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,016,975 A | 5/1991 | Sasaki et al. |
| 5,021,888 A | 6/1991 | Kondou et al. |
| 5,042,915 A | 8/1991 | Akutsu et al. |
| 5,065,444 A | 11/1991 | Garber |
| RE33,854 E | 3/1992 | Adair |
| 5,103,497 A | 4/1992 | Hicks |
| 5,111,804 A | 5/1992 | Funakoshi |
| 5,115,309 A | 5/1992 | Hang |
| 5,133,035 A | 7/1992 | Hicks |
| 5,168,361 A | 12/1992 | Hackmann |
| 5,168,863 A | 12/1992 | Kurtzer |
| 5,187,572 A | 2/1993 | Nakamura et al. |
| 5,188,094 A | 2/1993 | Adair |
| 5,200,838 A | 4/1993 | Nudelman et al. |
| 5,220,198 A | 6/1993 | Tsuji |
| 5,227,662 A | 7/1993 | Ohno et al. |
| 5,228,430 A | 7/1993 | Sakamoto |
| 5,237,403 A | 8/1993 | Sugimoto et al. |
| 5,241,170 A | 8/1993 | Field, Jr. et al. |
| 5,277,172 A | 1/1994 | Sugimoto |
| 5,289,555 A | 2/1994 | Sanso |
| 5,307,804 A | 5/1994 | Bonnet |
| 5,313,306 A | 5/1994 | Kuban et al. |
| 5,325,847 A | 7/1994 | Matsuno |
| 5,339,275 A | 8/1994 | Hyatt |
| 5,381,784 A | 1/1995 | Adair |
| 5,400,267 A | 3/1995 | Denen et al. |
| 5,402,768 A | 4/1995 | Adair |
| 5,411,020 A | 5/1995 | Ito |
| 5,427,087 A | 6/1995 | Ito et al. |
| 5,454,366 A | 10/1995 | Ito et al. |
| 5,461,425 A | 10/1995 | Fowler et al. |
| 5,471,515 A | 11/1995 | Fossum et al. |
| 5,489,801 A | 2/1996 | Blish, II |
| 5,494,483 A | 2/1996 | Adair |
| 5,522,006 A | 5/1996 | Takeuchi et al. |
| 5,550,595 A | 8/1996 | Hannah |
| 5,576,781 A | 11/1996 | Deleeuw |
| 5,594,282 A | 1/1997 | Otsuki |
| 5,594,497 A | 1/1997 | Ahern et al. |
| 5,614,763 A | 3/1997 | Womack |
| 5,665,959 A | 9/1997 | Fossum et al. |
| 5,721,422 A | 2/1998 | Bird |
| 5,734,418 A | 3/1998 | Danna |
| 5,748,234 A | 5/1998 | Lippincott |
| 5,754,313 A | 5/1998 | Pelchy et al. |
| 5,757,075 A | 5/1998 | Kitaoka |
| 5,784,099 A | 7/1998 | Lippincott |
| 5,787,298 A | 7/1998 | Broedner et al. |
| 5,841,126 A | 11/1998 | Fossum et al. |
| 5,857,963 A | 1/1999 | Pelchy et al. |
| 5,879,289 A | 3/1999 | Yarush et al. |
| 5,887,049 A | 3/1999 | Fossum |
| 5,896,166 A | 4/1999 | D'Alfonso et al. |
| 5,907,178 A | 5/1999 | Baker et al. |
| 5,929,901 A | 7/1999 | Adair et al. |
| 5,949,483 A | 9/1999 | Fossum et al. |
| 5,986,693 A | 11/1999 | Adair et al. |
| 5,990,506 A | 11/1999 | Fossum et al. |
| 6,005,619 A | 12/1999 | Fossum |
| 6,021,172 A | 2/2000 | Fossum et al. |
| 6,027,955 A | 2/2000 | Lee et al. |
| 6,028,330 A | 2/2000 | Lee et al. |
| 6,043,839 A | 3/2000 | Adair et al. |
| 6,059,776 A | 5/2000 | Gatto |
| 6,059,793 A | 5/2000 | Pagedas |
| 6,073,043 A | 6/2000 | Schneider |
| 6,096,573 A | 8/2000 | Chen |
| 6,101,232 A | 8/2000 | Fossum et al. |
| 6,118,142 A | 9/2000 | Chen et al. |
| 6,139,489 A | 10/2000 | Wampler et al. |
| 6,142,930 A | 11/2000 | Ito et al. |
| 6,144,542 A * | 11/2000 | Ker .............. H01L 27/0292 |
| | | 361/111 |
| 6,166,367 A | 12/2000 | Cho |
| 6,166,768 A | 12/2000 | Fossum et al. |
| 6,180,969 B1 | 1/2001 | Yang et al. |
| 6,184,055 B1 | 2/2001 | Yang et al. |
| 6,194,260 B1 | 2/2001 | Chien et al. |
| 6,198,087 B1 | 3/2001 | Boon |
| 6,207,984 B1 | 3/2001 | Chang |
| 6,211,904 B1 | 4/2001 | Adair et al. |
| 6,215,517 B1 | 4/2001 | Takahashi et al. |
| 6,239,456 B1 | 5/2001 | Berezin et al. |
| 6,242,277 B1 | 6/2001 | Lin et al. |
| 6,255,681 B1 | 7/2001 | Osadchy et al. |
| 6,272,269 B1 | 8/2001 | Naum |
| 6,275,255 B1 | 8/2001 | Adair et al. |
| 6,294,775 B1 | 9/2001 | Seibel et al. |
| 6,303,421 B1 | 10/2001 | Chang |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,327,493 B1 | 12/2001 | Ozawa et al. |
| 6,331,156 B1 | 12/2001 | Haefele et al. |
| 6,333,205 B1 | 12/2001 | Rhodes |
| 6,369,812 B1 | 4/2002 | Iyriboz et al. |
| 6,387,043 B1 | 5/2002 | Yoon |
| 6,388,243 B1 | 5/2002 | Berezin et al. |
| 6,390,972 B1 | 5/2002 | Speier et al. |
| 6,400,824 B1 | 6/2002 | Mansoorian et al. |
| 6,404,048 B2 | 6/2002 | Akram |
| 6,410,377 B1 | 6/2002 | Hwang et al. |
| 6,416,463 B1 | 7/2002 | Tsuzuki et al. |
| 6,419,626 B1 | 7/2002 | Yoon |
| 6,419,627 B1 | 7/2002 | Ben Nun |
| 6,424,369 B1 | 7/2002 | Adair et al. |
| 6,436,032 B1 | 8/2002 | Eto et al. |
| 6,441,482 B1 | 8/2002 | Foster |
| 6,452,626 B1 | 9/2002 | Adair et al. |
| 6,456,326 B2 | 9/2002 | Fossum et al. |
| 6,469,739 B1 | 10/2002 | Bechtel et al. |
| 6,485,414 B1 | 11/2002 | Neuberger |
| 6,512,280 B2 | 1/2003 | Chen et al. |

(56) References Cited

U.S. PATENT DOCUMENTS

| | | |
|---|---|---|
| 6,515,321 B1 | 2/2003 | Jwo |
| 6,549,235 B1 | 4/2003 | Fossum et al. |
| 6,555,842 B1 | 4/2003 | Fossum et al. |
| 6,570,617 B2 | 5/2003 | Fossum et al. |
| 6,588,884 B1 | 7/2003 | Furlani et al. |
| 6,606,122 B1 | 8/2003 | Shaw et al. |
| 6,610,557 B2 | 8/2003 | Lee et al. |
| 6,627,474 B2 | 9/2003 | Barna et al. |
| 6,659,940 B2 | 12/2003 | Adler |
| 6,665,013 B1 | 12/2003 | Fossum et al. |
| 6,690,466 B2 | 2/2004 | Miller et al. |
| 6,692,431 B2 | 2/2004 | Kazakevich |
| 6,704,049 B1 | 3/2004 | Fossum |
| 6,720,810 B1 | 4/2004 | New |
| 6,726,620 B2 | 4/2004 | Shibata et al. |
| 6,730,900 B2 | 5/2004 | Hsish et al. |
| 6,740,870 B1 | 5/2004 | Doudoumopoulos |
| 6,744,068 B2 | 6/2004 | Fossum et al. |
| 6,773,392 B2 | 8/2004 | Kikuchi et al. |
| 6,784,940 B1 | 8/2004 | Takazawa et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,812,949 B1 | 11/2004 | Switzer et al. |
| 6,838,653 B2 | 1/2005 | Campbell et al. |
| 6,838,716 B2 | 1/2005 | Asada et al. |
| 6,856,712 B2 | 2/2005 | Fauver et al. |
| 6,862,036 B2 | 3/2005 | Adair et al. |
| 6,879,340 B1 | 4/2005 | Chevallier |
| 6,897,082 B2 | 5/2005 | Rhodes et al. |
| 6,899,675 B2 | 5/2005 | Cline et al. |
| 6,921,920 B2 | 7/2005 | Kazakevich |
| 6,943,838 B2 | 9/2005 | Komoro et al. |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,976,954 B2 | 12/2005 | Takahashi |
| 6,982,740 B2 | 1/2006 | Adair et al. |
| 6,982,742 B2 | 1/2006 | Adair et al. |
| 6,997,871 B2 | 2/2006 | Sonnenschein et al. |
| 6,999,118 B2 | 2/2006 | Suzuki |
| 7,002,231 B2 | 2/2006 | Rhodes et al. |
| 7,002,621 B2 | 2/2006 | Adair et al. |
| 7,009,634 B2 | 3/2006 | Iddan et al. |
| 7,009,646 B1 | 3/2006 | Fossum et al. |
| 7,018,331 B2 | 3/2006 | Chang et al. |
| 7,027,092 B2 | 4/2006 | Altree |
| 7,030,904 B2 | 4/2006 | Adair et al. |
| 7,037,259 B2 | 5/2006 | Hakamata et al. |
| 7,061,117 B2 | 6/2006 | Yang et al. |
| 7,068,878 B2 | 6/2006 | Crossman-Bosworth et al. |
| 7,070,560 B2 | 7/2006 | Takashi et al. |
| 7,088,398 B1 | 8/2006 | Wolf et al. |
| 7,102,682 B2 | 9/2006 | Baer |
| 7,105,371 B2 | 9/2006 | Fossum et al. |
| 7,106,367 B2 | 9/2006 | Sarwari |
| 7,106,377 B2 | 9/2006 | Bean et al. |
| 7,115,091 B2 | 10/2006 | Root et al. |
| 7,129,108 B2 | 10/2006 | Jang |
| 7,183,129 B2 | 2/2007 | Lee |
| 7,184,084 B2 | 2/2007 | Glenn |
| 7,189,226 B2 | 3/2007 | Auld et al. |
| 7,193,519 B2 | 3/2007 | Root et al. |
| 7,202,899 B2 | 4/2007 | Lin et al. |
| 7,217,967 B2 | 5/2007 | Han |
| 7,227,469 B2 | 6/2007 | Varner et al. |
| 7,230,247 B2 | 6/2007 | Shibayama |
| 7,230,615 B2 | 6/2007 | Wang et al. |
| 7,232,712 B2 | 6/2007 | Han |
| 7,244,920 B2 | 7/2007 | Kim et al. |
| 7,250,594 B2 | 7/2007 | Lin et al. |
| 7,258,546 B2 | 8/2007 | Beier et al. |
| 7,258,663 B2 | 8/2007 | Doguchi et al. |
| 7,261,687 B2 | 8/2007 | Yang |
| 7,273,452 B2 | 9/2007 | Barbato et al. |
| 7,274,390 B2 | 9/2007 | Sevat et al. |
| 7,276,785 B2 | 10/2007 | Bauer et al. |
| 7,280,139 B2 | 10/2007 | Pahr et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 12/2007 | Couvillon, Jr. |
| 7,317,955 B2 | 1/2008 | McGreevy |
| 7,319,478 B2 | 1/2008 | Dolt et al. |
| 7,331,523 B2 | 2/2008 | Meier et al. |
| 7,338,832 B2 | 3/2008 | Park et al. |
| 7,339,982 B2 | 3/2008 | Wood, Jr. |
| 7,354,841 B2 | 4/2008 | Jeon |
| 7,365,768 B1 | 4/2008 | Ono et al. |
| 7,368,771 B2 | 5/2008 | Roh et al. |
| 7,369,166 B2 | 5/2008 | Fossum et al. |
| 7,369,176 B2 | 5/2008 | Sonnenschein et al. |
| 7,386,084 B2 | 6/2008 | Yin |
| 7,391,013 B2 | 6/2008 | Johnston et al. |
| 7,397,076 B2 | 7/2008 | Jang |
| 7,402,811 B2 | 7/2008 | Hatanaka et al. |
| 7,443,296 B2 | 10/2008 | Mezhinsky et al. |
| 7,470,893 B2 | 12/2008 | Suzuki et al. |
| 7,488,637 B2 | 2/2009 | Kim |
| 7,511,257 B2 | 3/2009 | Lee et al. |
| 7,517,351 B2 | 4/2009 | Culp et al. |
| 7,522,341 B2 | 4/2009 | Mouli |
| 7,525,168 B2 | 4/2009 | Hsieh |
| 7,534,645 B2 | 5/2009 | Choi |
| 7,535,037 B2 | 5/2009 | Lyu |
| 7,540,645 B2 | 6/2009 | Kazakevich |
| 7,542,069 B2 | 6/2009 | Tashiro |
| 7,544,163 B2 | 6/2009 | MacKinnon et al. |
| 7,545,434 B2 | 6/2009 | Bean et al. |
| 7,551,059 B2 | 6/2009 | Farrier |
| 7,564,935 B2 | 7/2009 | Suzuki |
| 7,567,291 B2 | 7/2009 | Bechtel et al. |
| 7,568,619 B2 | 8/2009 | Todd et al. |
| 7,573,516 B2 | 8/2009 | Krymski et al. |
| 7,578,786 B2 | 8/2009 | Boulais et al. |
| 7,583,872 B2 | 9/2009 | Seibel et al. |
| 7,589,349 B2 | 9/2009 | Hong |
| 7,595,210 B2 | 9/2009 | Shim |
| 7,598,686 B2 | 10/2009 | Lys et al. |
| 7,599,439 B2 | 10/2009 | Lavelle et al. |
| 7,605,016 B2 | 10/2009 | Min |
| 7,608,874 B2 | 10/2009 | Lee et al. |
| 7,612,318 B2 | 11/2009 | Jeon |
| 7,615,808 B2 | 11/2009 | Pain et al. |
| 7,615,838 B2 | 11/2009 | Kim |
| 7,616,986 B2 | 11/2009 | Seibel et al. |
| 7,630,008 B2 | 12/2009 | Sarwari |
| 7,646,407 B2 | 1/2010 | Fossum et al. |
| 7,663,115 B2 | 2/2010 | Korthout et al. |
| 7,744,528 B2 | 6/2010 | Wallace et al. |
| 7,749,799 B2 | 7/2010 | Pain |
| 7,768,562 B2 | 8/2010 | Boemler |
| 7,794,394 B2 | 9/2010 | Frangioni |
| 7,795,650 B2 | 9/2010 | Eminoglu et al. |
| 7,800,192 B2 | 9/2010 | Venezia et al. |
| 7,801,584 B2 | 9/2010 | Iddan et al. |
| 7,830,434 B2 | 11/2010 | Li et al. |
| 7,868,283 B2 | 1/2011 | Mabuchi |
| 7,871,373 B2 | 1/2011 | Yamada |
| 7,880,662 B2 | 2/2011 | Bogaerts |
| 7,901,974 B2 | 3/2011 | Venezia et al. |
| 7,914,447 B2 | 3/2011 | Kanai |
| 7,916,193 B2 | 3/2011 | Fossum |
| 7,923,763 B2 | 4/2011 | Lauxtermann |
| 7,935,050 B2 | 5/2011 | Luanava et al. |
| 7,936,394 B2 | 5/2011 | Wu |
| 7,944,566 B2 | 5/2011 | Xie |
| 7,952,096 B2 | 5/2011 | Rhodes |
| 7,973,342 B2 | 7/2011 | Jeon |
| 7,995,123 B2 | 8/2011 | Lee et al. |
| 8,089,542 B2 | 1/2012 | Chevallier |
| 8,100,826 B2 | 1/2012 | MacKinnon et al. |
| 8,101,903 B2 | 1/2012 | Mokhnatyuk |
| 8,154,055 B2 | 4/2012 | Ha |

(56) References Cited

U.S. PATENT DOCUMENTS

| | | |
|---|---|---|
| 8,159,584 B2 | 4/2012 | Iwabuchi et al. |
| 8,193,541 B2 | 6/2012 | Maehara |
| 8,212,884 B2 | 7/2012 | Seibel et al. |
| 8,300,111 B2 | 10/2012 | Iwane |
| 8,317,689 B1 | 11/2012 | Remijan et al. |
| 8,382,662 B2 | 2/2013 | Soper et al. |
| 8,384,814 B2 | 2/2013 | Chevallier |
| 8,396,535 B2 | 3/2013 | Wang et al. |
| 8,405,748 B2 | 3/2013 | Mao et al. |
| 8,423,110 B2 | 4/2013 | Barbato et al. |
| 8,426,096 B2 | 4/2013 | Maezawa |
| 8,471,938 B2 | 6/2013 | Altice, Jr. et al. |
| 8,476,575 B2 | 7/2013 | Mokhnatyuk |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,582,011 B2 | 11/2013 | Dosluoglu |
| 8,602,971 B2 | 12/2013 | Farr |
| 8,614,754 B2 | 12/2013 | Fossum |
| 8,625,016 B2 | 1/2014 | Fossum et al. |
| 8,629,023 B2 | 1/2014 | Lee |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,733,660 B2 | 5/2014 | Wang et al. |
| 8,754,358 B2 | 6/2014 | Chou et al. |
| 8,797,434 B2 | 8/2014 | Lee et al. |
| 8,830,340 B2 | 9/2014 | Burt et al. |
| 8,836,834 B2 | 9/2014 | Hashimoto et al. |
| 8,854,517 B2 | 10/2014 | Honda et al. |
| 8,858,425 B2 | 10/2014 | Farr et al. |
| 8,885,034 B2 | 11/2014 | Adair et al. |
| 8,896,730 B2 | 11/2014 | Fossum |
| 8,952,312 B2 | 2/2015 | Blanquart et al. |
| 9,066,677 B2 | 6/2015 | Seto |
| 9,123,602 B2 | 9/2015 | Blanquart |
| 9,153,609 B2 | 10/2015 | Blanquart |
| 9,343,489 B2 | 5/2016 | Blanquart et al. |
| 9,763,566 B2 | 9/2017 | Blanquart |
| 9,907,459 B2 | 3/2018 | Blanquart |
| 10,517,469 B2 | 12/2019 | Blanquart et al. |
| 10,517,471 B2 | 12/2019 | Blanquart |
| 2001/0016804 A1* | 8/2001 | Cunningham ....... G09B 23/285 703/7 |
| 2001/0019361 A1 | 9/2001 | Savoye |
| 2001/0030744 A1 | 10/2001 | Chang |
| 2001/0041825 A1 | 11/2001 | Shibata et al. |
| 2001/0052930 A1 | 12/2001 | Adair et al. |
| 2002/0011809 A1 | 1/2002 | Hartge et al. |
| 2002/0017611 A1 | 2/2002 | Tashiro et al. |
| 2002/0044207 A1 | 4/2002 | Dielhof et al. |
| 2002/0067408 A1 | 6/2002 | Adair et al. |
| 2002/0080248 A1 | 6/2002 | Adair et al. |
| 2002/0158986 A1 | 10/2002 | Baer |
| 2002/0163578 A1 | 11/2002 | Adair et al. |
| 2002/0180867 A1 | 12/2002 | Adair et al. |
| 2003/0007087 A1 | 1/2003 | Hakamata et al. |
| 2003/0043264 A1 | 3/2003 | Furuya et al. |
| 2003/0052983 A1 | 3/2003 | Altree |
| 2003/0107664 A1 | 6/2003 | Suzuki |
| 2003/0163029 A1 | 8/2003 | Sonnenschein et al. |
| 2003/0187586 A1 | 10/2003 | Katzenmaier et al. |
| 2003/0189663 A1 | 10/2003 | Dolt et al. |
| 2003/0218120 A1 | 11/2003 | Shibayama |
| 2004/0010196 A1 | 1/2004 | Wang et al. |
| 2004/0036010 A1 | 2/2004 | Hsieh et al. |
| 2004/0049215 A1 | 3/2004 | Snow et al. |
| 2004/0073086 A1 | 4/2004 | Abe |
| 2004/0078494 A1 | 4/2004 | Lennox et al. |
| 2004/0082833 A1 | 4/2004 | Adler et al. |
| 2004/0095495 A1 | 5/2004 | Inokuma et al. |
| 2004/0111012 A1 | 6/2004 | Whitman |
| 2004/0169771 A1 | 9/2004 | Washington et al. |
| 2004/0249267 A1 | 12/2004 | Gilboa |
| 2005/0027164 A1 | 2/2005 | Barbato et al. |
| 2005/0038322 A1 | 2/2005 | Banik |
| 2005/0075538 A1 | 4/2005 | Banik et al. |
| 2005/0131279 A1 | 6/2005 | Boulais et al. |
| 2005/0148819 A1 | 7/2005 | Noguchi et al. |
| 2005/0151866 A1 | 7/2005 | Ando et al. |
| 2005/0168941 A1 | 8/2005 | Sokol et al. |
| 2005/0174428 A1 | 8/2005 | Abe |
| 2005/0206755 A1 | 9/2005 | Yokoyama et al. |
| 2005/0222499 A1 | 10/2005 | Banik et al. |
| 2005/0231591 A1 | 10/2005 | Abe |
| 2005/0234302 A1 | 10/2005 | MacKinnon et al. |
| 2005/0237412 A1 | 10/2005 | Shiohara et al. |
| 2005/0288546 A1 | 12/2005 | Sonnenschein et al. |
| 2006/0007507 A1 | 1/2006 | Inaba et al. |
| 2006/0022234 A1 | 2/2006 | Adair et al. |
| 2006/0023109 A1 | 2/2006 | Mabuchi et al. |
| 2006/0035415 A1 | 2/2006 | Wood et al. |
| 2006/0069314 A1 | 3/2006 | Farr |
| 2006/0074289 A1 | 4/2006 | Adler et al. |
| 2006/0164533 A1 | 7/2006 | Hsieh et al. |
| 2006/0181627 A1 | 8/2006 | Farrier |
| 2006/0221230 A1 | 10/2006 | Dutta et al. |
| 2006/0249765 A1 | 11/2006 | Hsieh |
| 2006/0250513 A1 | 11/2006 | Yamamoto et al. |
| 2006/0293563 A1 | 12/2006 | Banik et al. |
| 2006/0293565 A1 | 12/2006 | Uchimura et al. |
| 2007/0002134 A1 | 1/2007 | Ishihara et al. |
| 2007/0030262 A1 | 2/2007 | Ambo et al. |
| 2007/0030345 A1 | 2/2007 | Amling et al. |
| 2007/0046803 A1 | 3/2007 | Ahn |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0129601 A1 | 6/2007 | Johnston et al. |
| 2007/0138375 A1 | 6/2007 | Lee et al. |
| 2007/0153337 A1 | 7/2007 | Kim |
| 2007/0159526 A1 | 7/2007 | Abe |
| 2007/0182842 A1 | 8/2007 | Sonnenschein et al. |
| 2007/0185549 A1 | 8/2007 | Zdeblick |
| 2007/0187703 A1 | 8/2007 | Erchak |
| 2007/0197873 A1 | 8/2007 | Birnkrant |
| 2007/0225556 A1 | 9/2007 | Ortiz et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0297190 A1 | 12/2007 | Ng |
| 2008/0021271 A1 | 1/2008 | Pasero et al. |
| 2008/0042046 A1 | 2/2008 | Mabuchi |
| 2008/0045800 A2 | 2/2008 | Farr |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0165360 A1 | 7/2008 | Johnston |
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0239124 A1 | 10/2008 | Mori et al. |
| 2008/0249369 A1 | 10/2008 | Seibel et al. |
| 2008/0255416 A1 | 10/2008 | Gilboa |
| 2008/0258042 A1 | 10/2008 | Krymski |
| 2008/0287798 A1 | 11/2008 | Lee et al. |
| 2008/0291290 A1 | 11/2008 | Sonoda et al. |
| 2008/0309810 A1 | 12/2008 | Smith et al. |
| 2008/0316319 A1 | 12/2008 | Nomoto |
| 2009/0012361 A1 | 1/2009 | MacKinnon et al. |
| 2009/0012368 A1 | 1/2009 | Banik |
| 2009/0015301 A1 | 1/2009 | Marchesini et al. |
| 2009/0021628 A1 | 1/2009 | Tamakoshi |
| 2009/0040783 A1 | 2/2009 | Krupa et al. |

(56) References Cited

U.S. PATENT DOCUMENTS

| | | |
|---|---|---|
| 2009/0054908 A1 | 2/2009 | Zand et al. |
| 2009/0062656 A1 | 3/2009 | Hyuga |
| 2009/0074265 A1 | 3/2009 | Huang et al. |
| 2009/0076329 A1 | 3/2009 | Su et al. |
| 2009/0082630 A1 | 3/2009 | Tulley |
| 2009/0091641 A1 | 4/2009 | Hattori |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0154886 A1 | 6/2009 | Lewis et al. |
| 2009/0160976 A1 | 6/2009 | Chen et al. |
| 2009/0160979 A1 | 6/2009 | Xu et al. |
| 2009/0173974 A1 | 7/2009 | Shah et al. |
| 2009/0184349 A1 | 7/2009 | Dungan |
| 2009/0186780 A1 | 7/2009 | Lee et al. |
| 2009/0192390 A1 | 7/2009 | Berguer et al. |
| 2009/0200624 A1 | 8/2009 | Dai et al. |
| 2009/0200625 A1 | 8/2009 | Venezia et al. |
| 2009/0203966 A1 | 8/2009 | Mizuyoshi |
| 2009/0208143 A1 | 8/2009 | Yoon et al. |
| 2009/0212397 A1 | 8/2009 | Tuttle |
| 2009/0216080 A1 | 8/2009 | Nakamura |
| 2009/0225548 A1 | 9/2009 | Narita |
| 2009/0230287 A1 | 9/2009 | Anderson et al. |
| 2009/0236500 A1 | 9/2009 | Shah et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0292168 A1 | 11/2009 | Farr |
| 2009/0306478 A1 | 12/2009 | Mizuyoshi |
| 2009/0316116 A1 | 12/2009 | Melville et al. |
| 2009/0322911 A1 | 12/2009 | Blanquart |
| 2009/0322912 A1 | 12/2009 | Blanquart |
| 2010/0026824 A1 | 2/2010 | Chen |
| 2010/0039156 A1* | 2/2010 | Yamaguchi .......... G09G 3/2096 327/291 |
| 2010/0059802 A1 | 3/2010 | Chen |
| 2010/0118932 A1 | 5/2010 | Luo et al. |
| 2010/0121142 A1 | 5/2010 | OuYang et al. |
| 2010/0134662 A1 | 6/2010 | Bub |
| 2010/0137684 A1 | 6/2010 | Shibasaki et al. |
| 2010/0140732 A1 | 6/2010 | Eminoglu et al. |
| 2010/0157037 A1 | 6/2010 | Iketani et al. |
| 2010/0157039 A1 | 6/2010 | Sugai |
| 2010/0157117 A1 | 6/2010 | Wang |
| 2010/0178722 A1 | 7/2010 | de Graff et al. |
| 2010/0182446 A1 | 7/2010 | Matsubayashi |
| 2010/0194860 A1 | 8/2010 | Mentz et al. |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2010/0245647 A1 | 9/2010 | Honda et al. |
| 2010/0276572 A1 | 11/2010 | Iwabuchi et al. |
| 2010/0290100 A1 | 11/2010 | Karasawa |
| 2010/0295978 A1 | 11/2010 | Nakamura et al. |
| 2010/0305406 A1 | 12/2010 | Braun et al. |
| 2010/0315333 A1* | 12/2010 | Hsu ...................... G06F 3/0383 345/157 |
| 2011/0028790 A1 | 2/2011 | Farr et al. |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0049591 A1 | 3/2011 | Nakatani et al. |
| 2011/0050874 A1 | 3/2011 | Reshef et al. |
| 2011/0050969 A1 | 3/2011 | Nishihara |
| 2011/0055447 A1 | 3/2011 | Costa |
| 2011/0063428 A1 | 3/2011 | Sonnenschein et al. |
| 2011/0115663 A1 | 5/2011 | Bogaerts |
| 2011/0121654 A1* | 5/2011 | Recker .................... H02J 9/065 307/66 |
| 2011/0128408 A1 | 6/2011 | Ishigaki et al. |
| 2011/0181840 A1 | 7/2011 | Cobb |
| 2011/0208004 A1 | 8/2011 | Feingold et al. |
| 2011/0237882 A1 | 9/2011 | Saito |
| 2011/0237884 A1 | 9/2011 | Saito |
| 2011/0238977 A1 | 9/2011 | Talbert et al. |
| 2011/0242300 A1 | 10/2011 | Hashimoto |
| 2011/0245605 A1 | 10/2011 | Jacobsen et al. |
| 2011/0263941 A1 | 10/2011 | Wright et al. |
| 2011/0288374 A1 | 11/2011 | Hadani et al. |
| 2011/0295061 A1 | 12/2011 | Haramaty et al. |
| 2011/0298908 A1 | 12/2011 | Murakami |
| 2012/0004508 A1 | 1/2012 | McDowall et al. |
| 2012/0029279 A1 | 2/2012 | Kucklick |
| 2012/0035419 A1 | 2/2012 | Ashida et al. |
| 2012/0035434 A1 | 2/2012 | Ferren et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0071720 A1* | 3/2012 | Banik ................. A61B 1/00059 600/118 |
| 2012/0078052 A1 | 3/2012 | Cheng |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0147229 A1 | 6/2012 | Shah et al. |
| 2012/0265196 A1 | 10/2012 | Turner et al. |
| 2012/0293699 A1 | 11/2012 | Blanquart et al. |
| 2012/0307030 A1 | 12/2012 | Blanquart |
| 2013/0010166 A1 | 1/2013 | Morisaki et al. |
| 2013/0126707 A1 | 5/2013 | Blanquart |
| 2013/0126708 A1 | 5/2013 | Blanquart |
| 2013/0126709 A1 | 5/2013 | Blanquart |
| 2013/0144122 A1 | 6/2013 | Adair et al. |
| 2013/0158346 A1 | 6/2013 | Soper et al. |
| 2013/0176409 A1 | 7/2013 | Kotani et al. |
| 2013/0222165 A1 | 8/2013 | David et al. |
| 2013/0242069 A1 | 9/2013 | Kobayashi |
| 2013/0264465 A1* | 10/2013 | Dai .................... H01L 27/14601 250/208.1 |
| 2013/0292854 A1 | 11/2013 | Lua et al. |
| 2013/0300837 A1 | 11/2013 | DiCarlo et al. |
| 2014/0052004 A1 | 2/2014 | D'Alfonso et al. |
| 2014/0073852 A1 | 3/2014 | Banik et al. |
| 2014/0104466 A1 | 4/2014 | Fossum |
| 2014/0160259 A1 | 6/2014 | Blanquart et al. |
| 2014/0175591 A1 | 6/2014 | Tian et al. |
| 2014/0198240 A1 | 7/2014 | Rhoads |
| 2014/0203084 A1 | 7/2014 | Wang |
| 2014/0217268 A1 | 8/2014 | Schleipen et al. |
| 2014/0267851 A1 | 9/2014 | Rhoads |
| 2014/0285645 A1 | 9/2014 | Blanquart et al. |
| 2014/0300698 A1 | 10/2014 | Wany |
| 2014/0354788 A1 | 12/2014 | Yano |
| 2014/0364689 A1 | 12/2014 | Adair et al. |
| 2015/0215560 A1 | 7/2015 | Blanquart et al. |
| 2016/0155765 A1 | 6/2016 | Blanquart |
| 2016/0190197 A1 | 6/2016 | Blanquart |
| 2016/0256041 A1 | 9/2016 | Blanquart et al. |
| 2017/0221945 A1 | 8/2017 | Blanquart |
| 2019/0007588 A1 | 1/2019 | Blanquart et al. |
| 2019/0008375 A1 | 1/2019 | Blanquart et al. |
| 2019/0068909 A1 | 2/2019 | Kaibara |
| 2019/0269304 A1 | 9/2019 | Blanquart |

FOREIGN PATENT DOCUMENTS

| | | |
|---|---|---|
| CN | 1398407 A | 2/2003 |
| CN | 1953193 A | 4/2007 |
| CN | 1992821 A | 7/2007 |
| CN | 100407433 C | 7/2008 |
| CN | 101214154 A | 7/2008 |
| CN | 101281918 A | 10/2008 |
| CN | 100502024 C | 6/2009 |
| CN | 101640211 A | 2/2010 |
| CN | 101013714 A | 5/2010 |
| CN | 101715644 A | 5/2010 |
| CN | 101848344 A | 9/2010 |
| CN | 101939841 A | 1/2011 |
| CN | 101978598 A | 2/2011 |
| CN | 102006427 A | 4/2011 |
| CN | 102266217 A | 12/2011 |
| CN | 102397049 A | 4/2012 |

(56) References Cited

FOREIGN PATENT DOCUMENTS

| | | |
|---|---|---|
| CN | 102450998 A | 5/2012 |
| CN | 103094653 A | 5/2013 |
| CN | 103636000 A | 3/2014 |
| CN | 103650476 A | 3/2014 |
| EP | 1618833 A1 | 1/2006 |
| EP | 1628348 A1 | 2/2006 |
| EP | 2108305 A1 | 10/2009 |
| EP | 2234387 A1 | 9/2010 |
| EP | 2302905 A1 | 3/2011 |
| EP | 2442558 A1 | 4/2012 |
| EP | 1845835 B1 | 11/2014 |
| GB | 2463866 A | 3/2010 |
| IL | 229396 | 7/2016 |
| IL | 229397 | 7/2016 |
| JP | 2012-030004 | 5/1995 |
| JP | H05-268534 | 5/1995 |
| JP | H09-140664 | 12/1998 |
| JP | 2001339057 | 7/2001 |
| JP | 2002-329851 | 11/2002 |
| JP | 2004-241490 A | 8/2004 |
| JP | 2004-348676 A | 12/2004 |
| JP | 2006-025852 | 2/2006 |
| JP | 2006-049361 | 2/2006 |
| JP | 2007-043433 A | 2/2007 |
| JP | 2007-214191 A | 8/2007 |
| JP | 2007-214772 A | 8/2007 |
| JP | 2007-228460 | 9/2007 |
| JP | 2008-235478 | 10/2008 |
| JP | 2008-290817 | 12/2008 |
| JP | 2009-005329 A | 1/2009 |
| JP | 2009-100380 A | 5/2009 |
| JP | 2009206958 A | 9/2009 |
| JP | 2010-200109 A | 9/2010 |
| JP | 2010-252396 | 11/2010 |
| JP | 2010-273757 | 12/2010 |
| JP | 2011-050969 A | 3/2011 |
| JP | 2011-114733 A | 6/2011 |
| JP | 1993-268534 A | 2/2012 |
| KR | 20100106920 | 10/2010 |
| KR | 20100126749 | 12/2010 |
| WO | 9413191 | 6/1994 |
| WO | 1996005693 A1 | 2/1996 |
| WO | 200108549 A1 | 2/2001 |
| WO | 2004093438 | 10/2004 |
| WO | 2006080015 A2 | 8/2006 |
| WO | 2006129762 A1 | 12/2006 |
| WO | 2009135255 | 11/2009 |
| WO | 2012155142 A1 | 11/2012 |
| WO | 2012155143 A1 | 11/2012 |
| WO | 2012155150 A1 | 11/2012 |
| WO | 2012155152 A1 | 11/2012 |
| WO | 2014018948 A2 | 1/2014 |
| WO | 2014145246 A1 | 9/2014 |
| ZA | 2012800337461 | 5/2012 |

\* cited by examiner

Switch cap voltage up-convertor

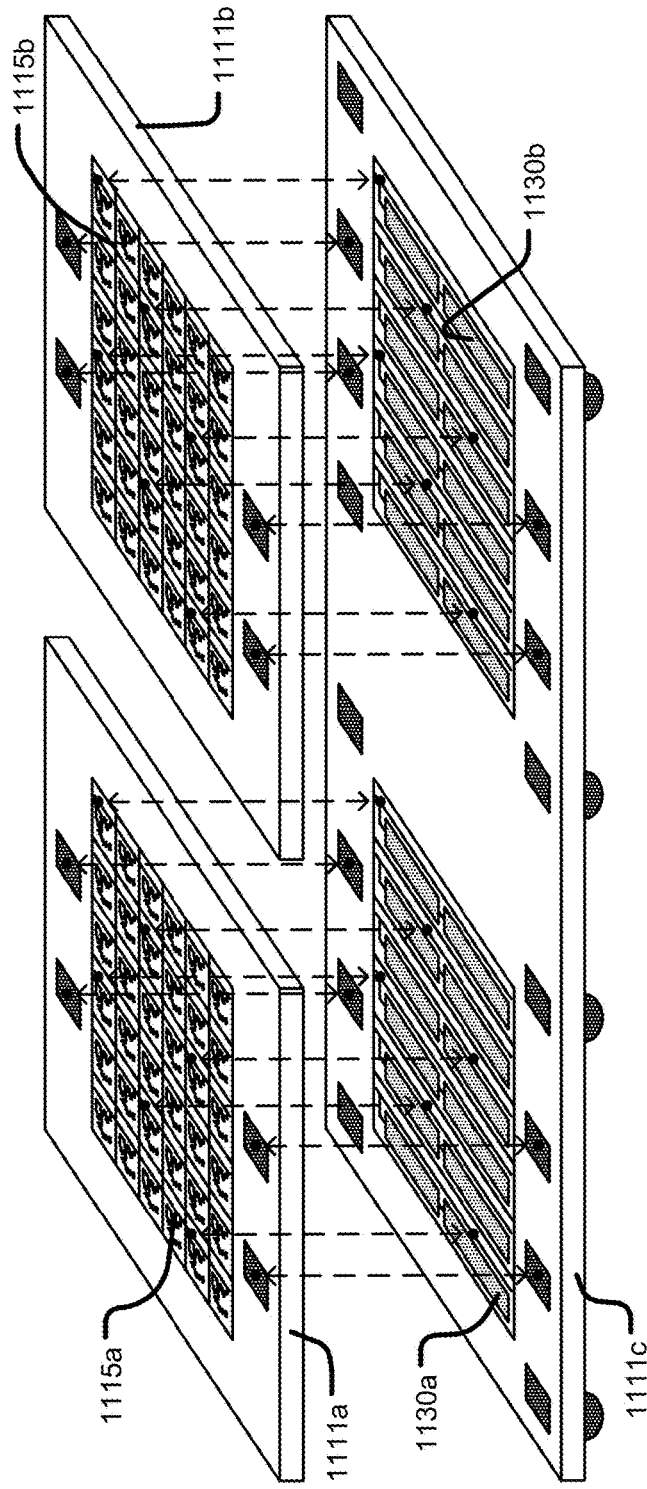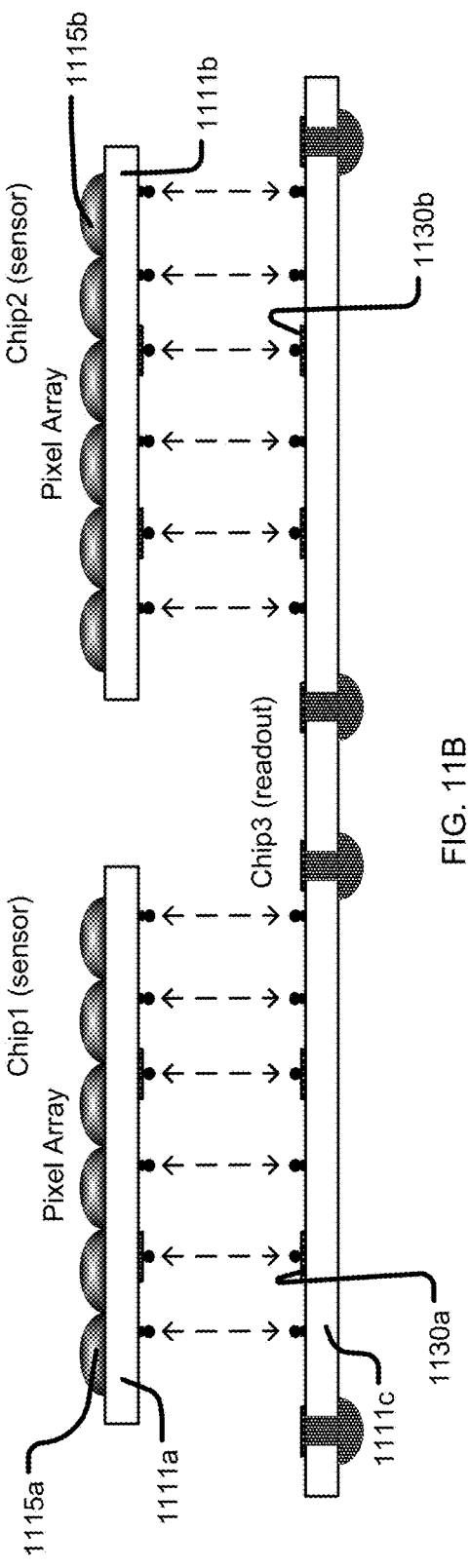
FIG. 11A
FIG. 11B

MINIMIZE IMAGE SENSOR I/O AND CONDUCTOR COUNTS IN ENDOSCOPE APPLICATIONS

CROSS-REFERENCE TO RELATED APPLICATIONS

This application claims the benefit of U.S. Provisional Application No. 61/791,547, filed Mar. 15, 2013, and U.S. Provisional Application No. 61/790,590, filed Mar. 15, 2013, both of which are hereby incorporated by reference herein in their entireties, including but not limited to those portions that specifically appear hereinafter, the incorporation by reference being made with the following exception: In the event that any portion of any of the above-referenced provisional applications is inconsistent with this application, this application supersedes said above-referenced provisional applications.

STATEMENT REGARDING FEDERALLY SPONSORED RESEARCH OR DEVELOPMENT

Not Applicable.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to minimizing the area and reducing the number of inputs and outputs of an image sensor for use in an endoscopic device. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings.

FIGS. 11A and 11B illustrate views of an implementation of an imaging sensor having a plurality of pixel arrays for producing a three dimensional image, wherein the plurality of pixel arrays and the image sensor are built on a plurality of substrates.

DETAILED DESCRIPTION

The disclosure extends to methods, systems, and computer based products for digital imaging that may be primarily suited to medical applications. In the following description of the disclosure, reference is made to the accompanying drawings, which form a part hereof, and in which is shown by way of illustration specific implementations in which the disclosure may be practiced. It is understood that other implementations may be utilized and structural changes may be made without departing from the scope of the disclosure.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "proximal" shall refer broadly to the concept of a portion nearest an origin.

As used herein, the term "distal" shall generally refer to the opposite of proximal, and thus to the concept of a portion farther from an origin, or a furthest portion, depending upon the context.

Figure 1:
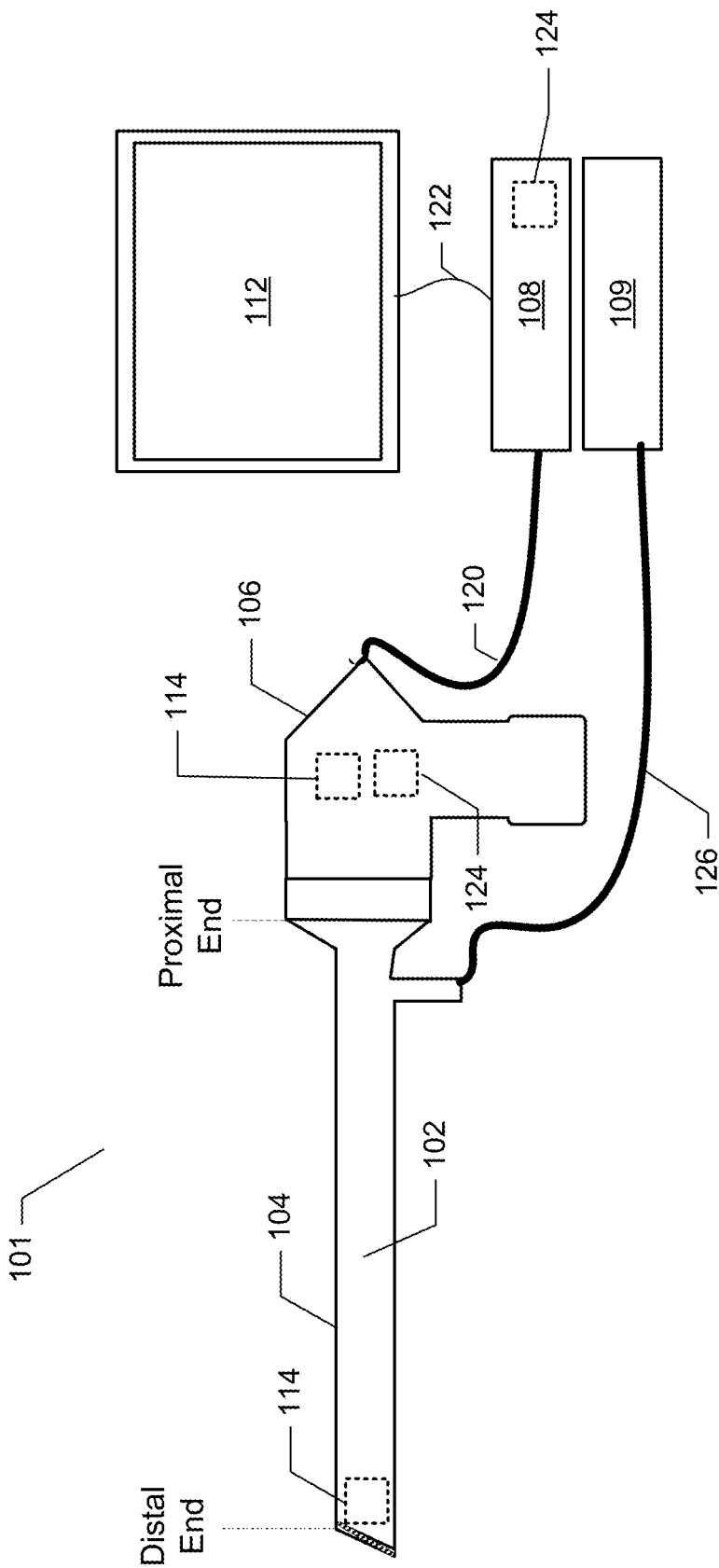
FIG. 1 illustrates an implementation of an endoscopic system in accordance with the principles and teachings of the disclosure.

Referring now to FIG. 1, there is illustrated a digital imaging system that utilizes minimal pad interconnects in order to reduce the size of the image sensor for use with an endoscopic device within a light deficient environment. The digital imaging system 101 illustrated in FIG. 1 may comprise an endoscopic device 102 for use in ambient light deficient environment. The endoscopic device 102, in turn, may include an endoscope 104, an endoscope housing 106 (e.g., hand piece and/or camera head), control unit 108, an electronic communication 120, such as an electronic cable, light source 109, a light cable 126, such as a fiber optic cable, connected to light source 109 and endoscopic device 102, display 112, and imaging device 114 (e.g., image sensor and related circuitry etc.). Note that in this example, to facilitate discussion, the endoscope device 104, endoscope housing 106, control unit 108, light source 109, display 112, and imaging device 114 are each shown individually with respect to one another. However, it is to be appreciated and understood that this is not to be interpreted as limiting, and any one or more of these components can be integrated and/or connected in any suitable way.

It will be appreciated that imaging device 114 may include an image sensor comprising a pixel array, wherein a scene is continuously focused onto the pixel array. It will be appreciated that the image sensor senses reflected electromagnetic radiation using or with the pixel array. The pixel array generates image data and an image frame is created from the image data. A processor 124 may detect image textures and edges within the image frame and may further enhance textures and edges within the image frame. The processor 124, whether in the housing 106 or at the control unit 108, may also retrieve from memory properties pertaining to the pixel technology and the applied sensor gain to assess an expectation for the magnitude of noise within an image frame created by said sensor and using said noise expectation to control the edge enhancement application. A stream of images may be created by sequentially combining a plurality of the image frames.

It will be appreciated that traditional rod-lens endoscopes, used for laparoscopy, arthroscopy, urology, gynecology and ENT (ear-nose-throat) procedures, are expensive to manufacture owing to their complex optical composition. The incident image information is transported in the optical domain all the way along its length. Typically it is optically coupled to a hand-piece unit, wherein the image sensing device(s) reside. This type of rigid endoscope is also delicate and prone to damage during handling, use and sterilization. The necessary repair and sterilization processes add further expense to each procedure for which they are utilized.

Advances in imaging technology have led to complementary metal-oxide semiconductor (CMOS) sensors that are cheap to manufacture and are highly customizable. Much of the external circuitry that was necessary to operate charge-coupled device (CCD) based sensors may be integrated into the same chip as the pixel array and lower operation voltages are needed. Therefore CMOS-based cameras are much cheaper and easier to manufacture and may be much more versatile than their CCD-based counterparts. For similar reasons, CMOS sensors are appearing more and more within endoscope systems.

Much cheaper endoscopes may be realized by placing the image sensing device at the distal end, since the optical transport assembly may be effectively replaced by a simple plastic lens stack, not dissimilar to what exists in a typical cell phone camera. They may be so inexpensive in fact that it may make more financial sense to have them be manufactured for single use only, to be subsequently disposed of or recycled, since that negates the repair and sterilization processes.

The difficulty in creating such an endoscope solution is in maintaining image quality since the region into which the sensor must fit is highly space constrained in both dimensions. Reducing the sensor area generally implies a reduction in pixel count and/or pixel area which may impact the resolution, sensitivity and dynamic range. Normally, endoscope systems are geared toward sensing steady broadband illumination and providing color information by segmenting the array into pixels of three or more ranges of wavelength sensitivity. This is done by crafting an individual color filter over each pixel, the Bayer mosaic being the most common solution. One way to avoid resolution loss is to eliminate the color filters since with the Bayer mosaic e.g. there may be up to a factor $1/\sqrt{2}$ loss in luminance resolution (in x or y) as compared with the native array resolution. The color information in such a case can be provided by pulsing a laser or LED-based illuminants with different wavelengths or combinations thereof during separate frame captures. Applicant has developed such systems and devices, which allow for high definition quality at progressive frame rates of 60 Hz or higher by virtue of a special sensor design. Additional developments by Applicant allow for the peripheral circuitry to be reduced to its minimal area while transmitting image data off chip in the digital domain.

It will be appreciated by those of skill in the art that each bond pad occupies significant physical space on a chip. Each bond pad is used to provide power or input/output signals to and from the sensor chip. Therefore in striving for minimal area it is desirable to reduce the number of bond pads as much as possible. This disclosure described a strategy for reducing pad count by combining digital input and output functionality into the same bi-directional pads. During image transmission they act as differential outputs. Then during a defined portion of each frame, they switch direction, in order to enable commands to be received. This requires that the camera control electronics have the commands issued to the sensor synchronized to the timing of the frame. This approach may be useful in the context of many CMOS sensor applications since sensor cost scales with chip area.

Another way to reduce the pad count described herein, is to use only a single external power supply and use, e.g., internal DC to DC converters or regulators to provide for multiple internal (e.g., analog and digital) supplies.

Further to this, in the context of an endoscope system, the simplicity and manufacturability can be enhanced by customizing the image sensor in order to receive commands and information from the endo scope hand-piece. The information may then be subsequently incorporated into the output data issued by the sensor. This reduces the overall conductor count from endoscope to camera system. Such information sources may include user instigated button events or measurements of the angle of rotation of the endoscope with respect to the hand-piece. Angular measurements are necessitated by certain embodiments of endoscopes having their image sensors placed at the distal end.

CMOS image sensors typically incorporate two different power supplies, necessitating three pads: VDD1, VDD2 & GND. The higher of the two voltages is used predominantly for the purpose of biasing the pixel array. Occasionally it will also be used to power input/output circuits. The lower voltage would typically be used to power the peripheral analog circuitry and the digital portion of the sensor, where applicable. Sometimes however, certain analog readout elements are powered using the higher supply voltage, which is usually in the range of about 3V to about 4V.

One strategy for reducing the pad count is to supply only a single power level and have the second one derived on-chip. This would also be effective in removing a power circuit (regulator etc.) from the camera system.

Figure 2:
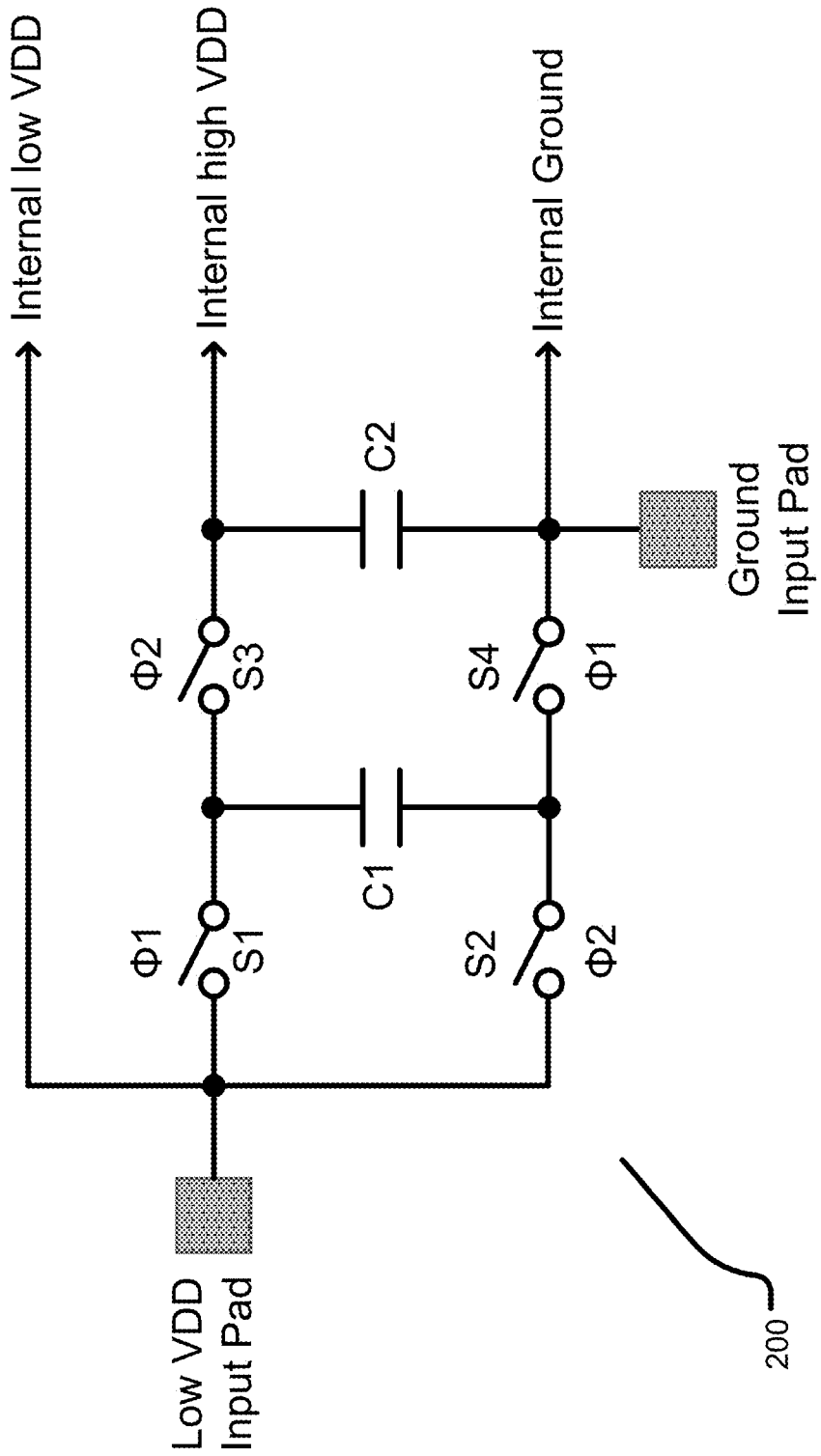
FIG. 2 illustrates an implementation of an internal up-conversion from a supplied low voltage to the higher voltage in accordance with the principles and teachings of the disclosure.

FIG. 2 illustrates one implementation of an internal up-conversion from a supplied low voltage to the higher voltage. This example is based upon a switch-cap DC-DC up-convertor 200. Both the flying cap (C1) and the decoupling cap (C2) are internal. The low power voltage (low VDD) supplies the up-convertor along with the relevant internal circuitry. It will be appreciated that an oscillator (not illustrated in FIG. 2) delivers the correct switching pattern to S1 through S4. This oscillator may be powered from the low voltage and proper level shifting needs to happen to have the correct switching voltage levels. The generated power supply may be tuned by carefully choosing the oscillator frequency, the internal resistance of the switch and the ratio between the flying cap and the decoupling cap (C1/C2).

Figure 3A:
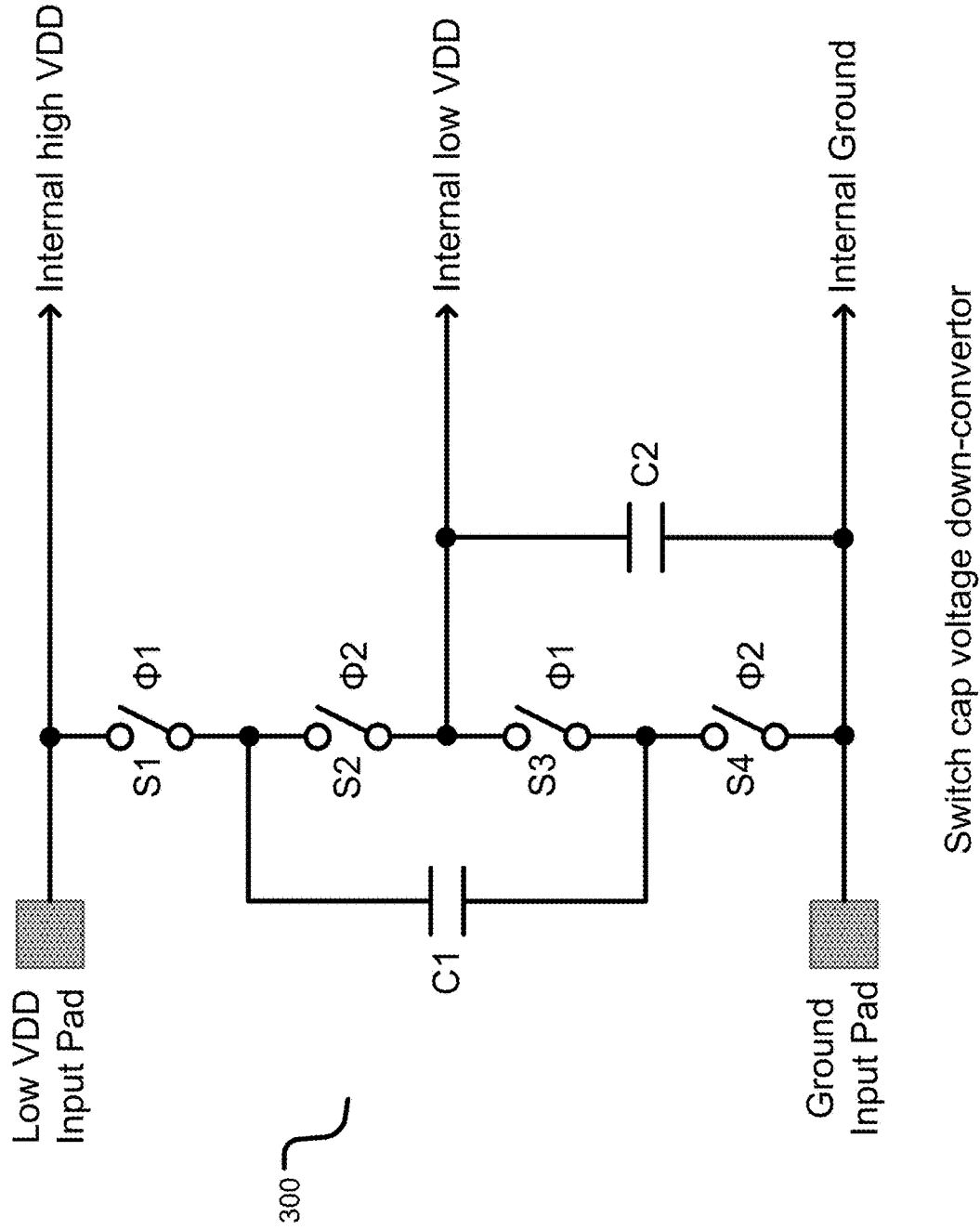
FIG. 3A illustrates an implementation of a down regulator that is based upon a switch-cap DC-DC down-convertor in accordance with the principles and teachings of the disclosure.
Figure 3B:
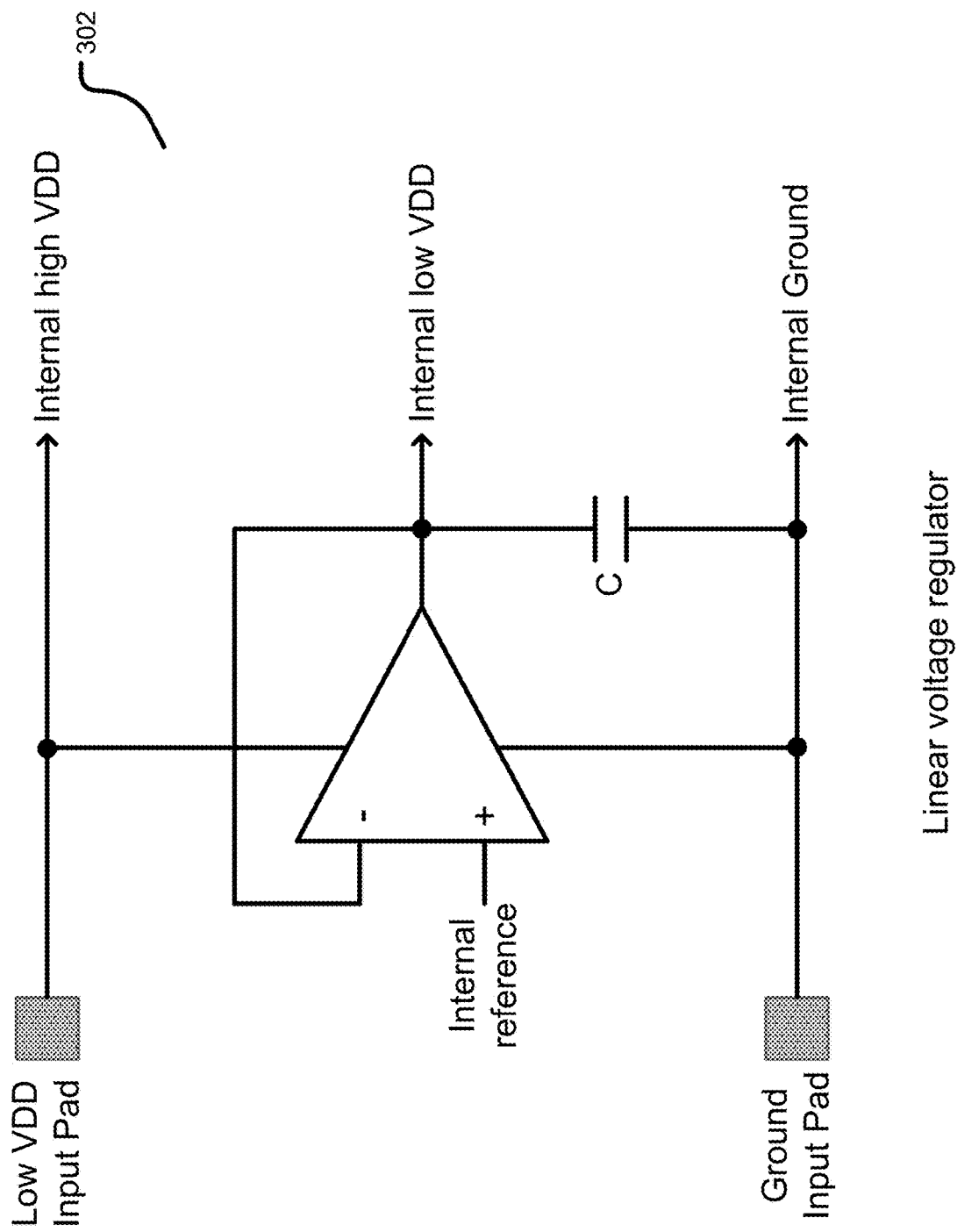
FIG. 3B illustrates an implementation of a down regulator that is based upon a Low Drop Out regulator in accordance with the principles and teachings of the disclosure.

In another implementation, the supplied voltage may be the high voltage supply (high VDD). FIGS. 3A and 3B depict two examples of a down regulator that may be used in this configuration. FIG. 3A illustrates a system that is based upon a switch-cap DC-DC down-convertor 300. It should be noted that in an implementation, similar considerations may be applied as for the convertor in FIG. 2.

FIG. 3B illustrates an implementation comprising a Low Drop Out regulator (LDO) 302 is based upon a linear circuit. The internal reference may come from a simple resistive divider or from a band gap reference generator. Although less susceptible to pick-up noise (as there are no switching elements), the LDO is often less efficient than its switch-cap counterpart.

It should be noted that in general, up-conversion may be used more readily than down regulators. This is because the sensor high voltage is usually less critical in terms of noise and requires less current consumption. Therefore the specifications for an up-converter are less demanding.

The CMOS image sensors of the disclosure may have a plurality of internal on-chip registers. These provide the sensor with flexibility and optimization options. The presence of these registers usually necessitates dedicated digital pads, in order that they may be configured using a defined slow-control protocol.

A system and method for eliminating or reducing these digital pads, while maintaining configurable registers may comprise the following. The system and method may be based on an approach that uses dual purpose pads for both input and output. These pads are designed to automatically switch between the output and input states at well-defined times. When the pads are acting as outputs, image data and other types of data are issued from the sensor. When the pads are in the input state they may receive slow control commands. To facilitate this, the frame period may be divided into three defined states, rolling-readout (image data is issued), service-lines (other types of data issued) and the configuration phase, during which the pads become inputs. The camera system needs to know what state the sensor pads are in at all times. During the rolling-readout and service-line phases, the camera system may not issue slow-control commands.

Figure 4:
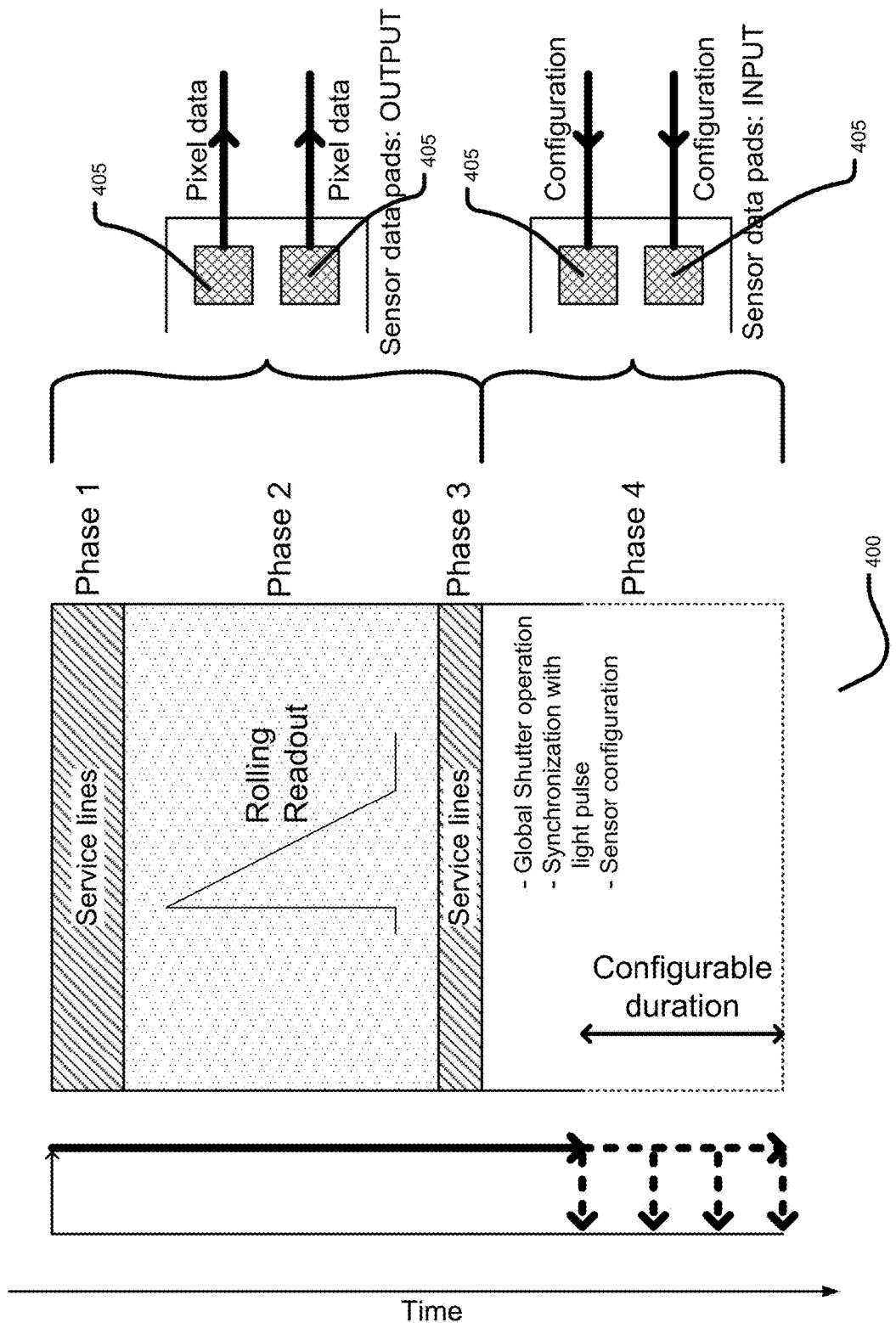
FIG. 4 illustrates an implementation of a frame timing structure in accordance with the principles and teachings of the disclosure.

FIG. 4 Illustrates an implementation of a method of timing. The frame timing structure 400 is depicted in FIG. 4 wherein the configuration and service-line phases are also used to pulse the light in pulsed illumination-based systems.

For reasons of cost, simplicity and manufacturability, it may be advantageous to conceive of an endoscope with a minimal number of conductors, with no active components other than the sensor, and a cable that solely incorporates the communication protocol between the sensor and the remainder of the camera system. When combined with bi-directional sensor data pads 405 and internal voltage generation (as per the methods described herein), the cable may be as minimal as having just as many data wires as needed to support the requisite image bandwidth and one power supply requiring just two wires (i.e., power and ground).

In a conventional modern endoscope, dedicated electrical connections may be needed for operations that are not directly related to the sensor. For example there are extra wires to service hand-piece buttons. These may be wires connected directly to the button, or alternatively to a local microcontroller that also serves also other functions.

In other examples, sensors may be needed to determine the angular position of the endoscope. The angle information should be relayed using various methods and structures to the image processing chain (ISP) within the camera system.

One strategy for reducing the endoscope conductor count is that any low speed analog and digital signals, instead of being sent directly to the camera system, may be re-routed to the CMOS image sensor. Within the sensor the signals may be digitally converted, if necessary, before being encoded alongside the image data or in lieu of pixel data within special service lines. Such as a strategy may eliminate the need for extra wires in the endoscope cable and extra active components within the endoscope hand-piece or lumen. Issuing the data at the sensor frame rate may also allow for increased (i.e., faster) system response. The camera system simply needs to decode this "hidden" information and act accordingly.

Figure 5:
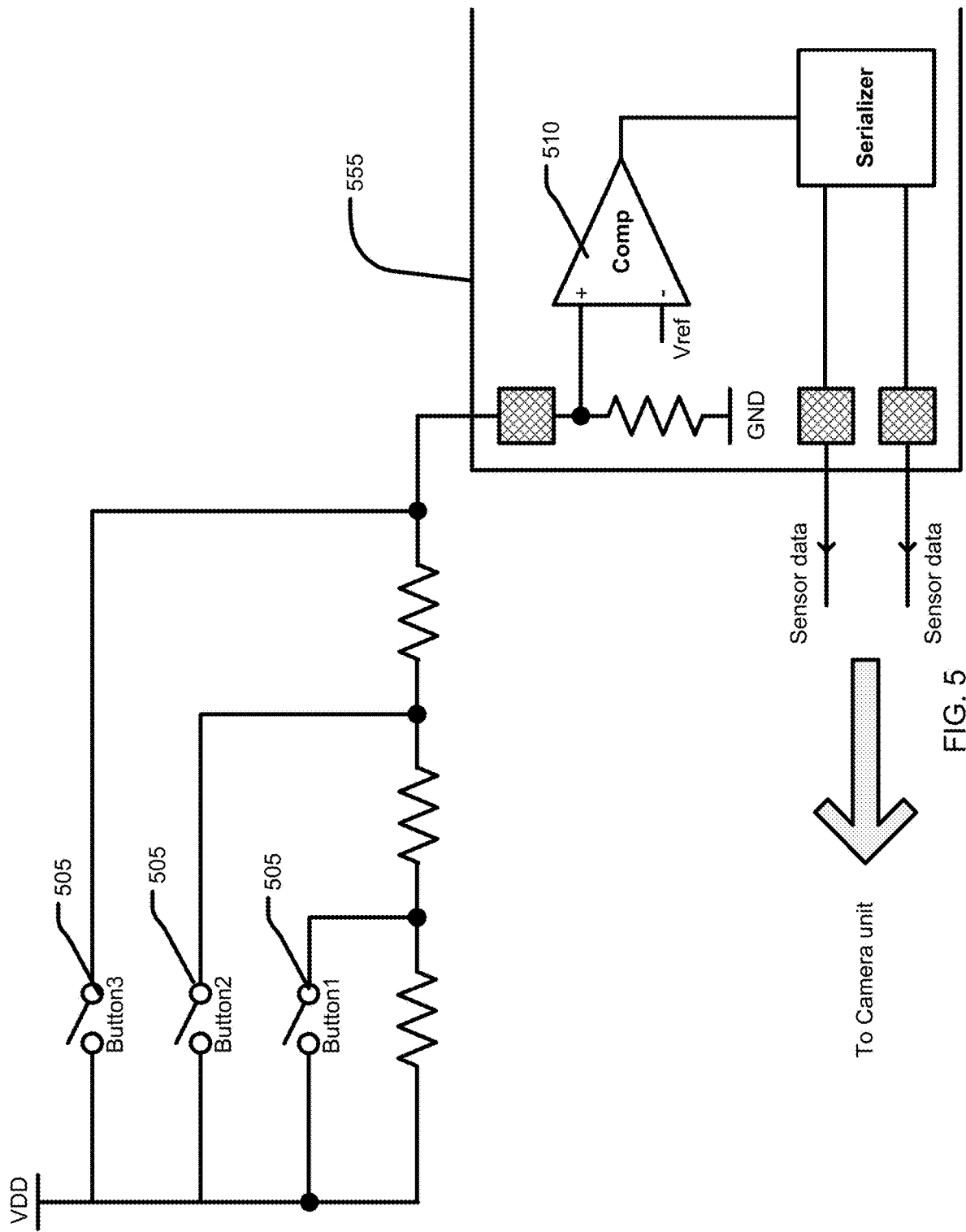
FIG. 5 illustrates an implementation of connections between endoscope buttons and a sensor based upon a resistance network in accordance with the principles and teachings of the disclosure.

FIG. 5 illustrates an implementation of connections between the endoscope buttons 505 and the sensor 555 based upon a resistance network. In this approach, a series of on-chip comparators 510 may convert the analog signal into a digital word ready to be issued as output data.

Figure 6:
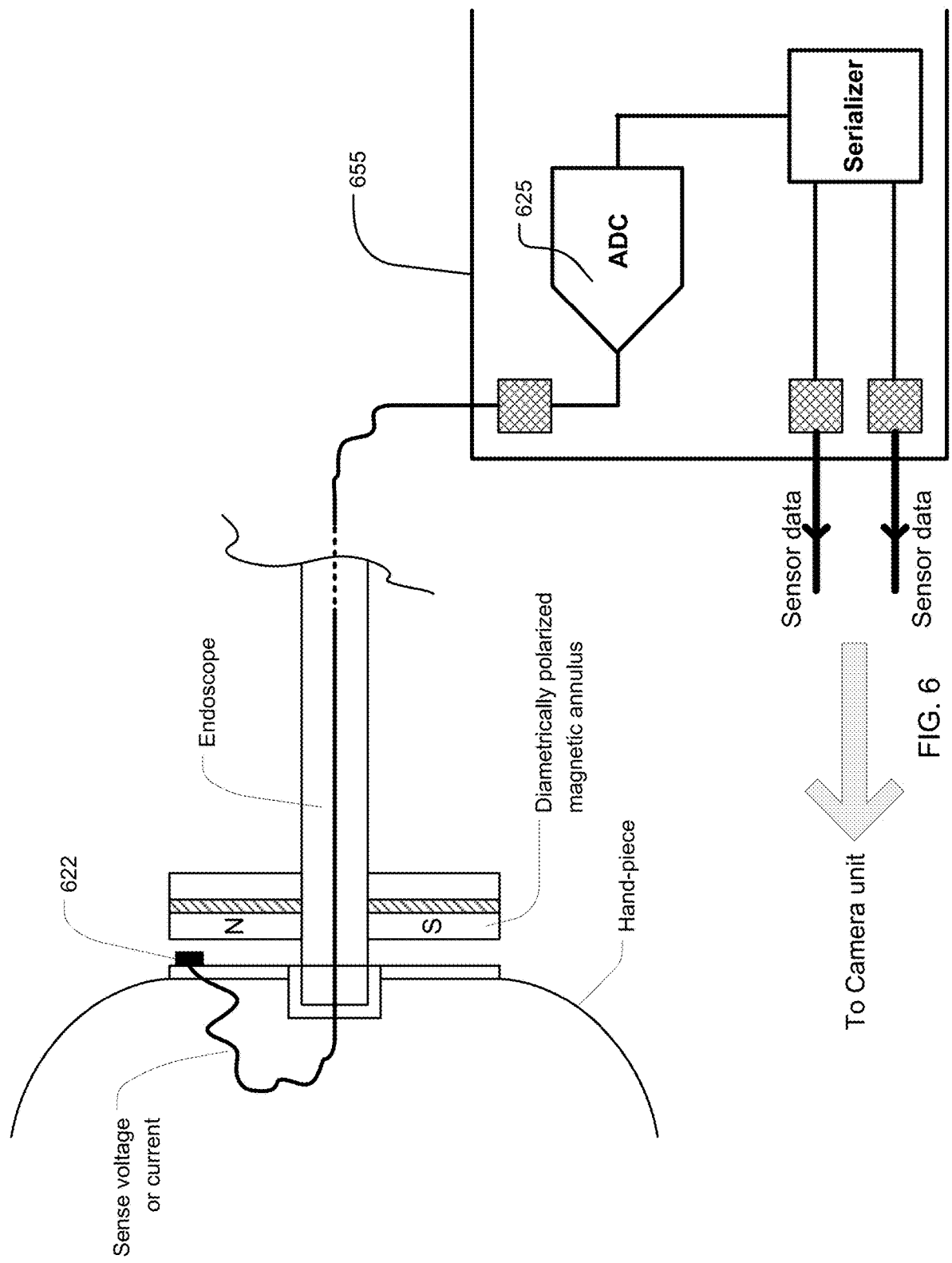
FIG. 6 illustrates an implementation in which an angular position Hall sensor delivers an analog voltage directly to a CMOS image sensor in accordance with the principles and teachings of the disclosure.

FIG. 6 illustrates an implementation in which an angular position Hall Effect sensor 622 delivers an analog voltage directly to the CMOS image sensor 655. In this case, the analog voltage may be converted by an on-chip analog-digital converter (ADC) and inserted within the frame.

Figure 7:
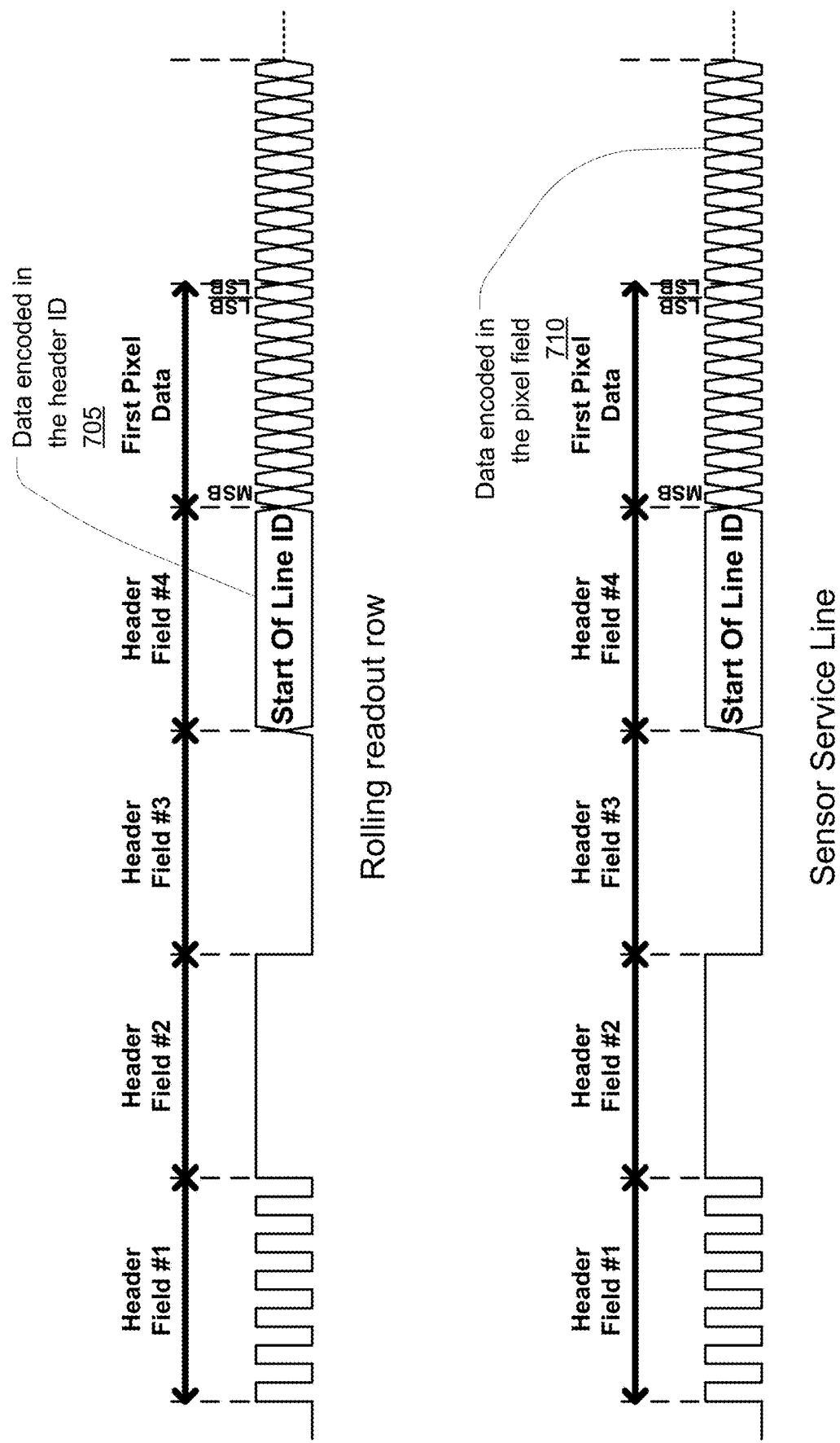
FIG. 7 illustrates implementations of encoding examples for digital data words within frame data in accordance with the principles and teachings of the disclosure.

FIG. 7 illustrates two possible encoding examples for digital data words within the frame data. They may be, for example, inserted in the row header 705 or by replacing "pixel" data within the service rows 710. It should be noted that there are multiple other configurations for encoding digital data words within the CMOS sensor image data and all such configurations are intended to fall within the scope of this disclosure.

It should also be noted that FIG. 5 and FIG. 6 are merely exemplary and other forms of data may be sent to the CMOS sensor other than that described above without departing from the scope of the disclosure. Such data comprises digital data for which case a serial communication protocol would serve the purpose well.

Implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. In an implementation, a sensor and camera control unit may be networked in order to communicate with each other, and other components, connected over the network to which they are connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Figure 8:
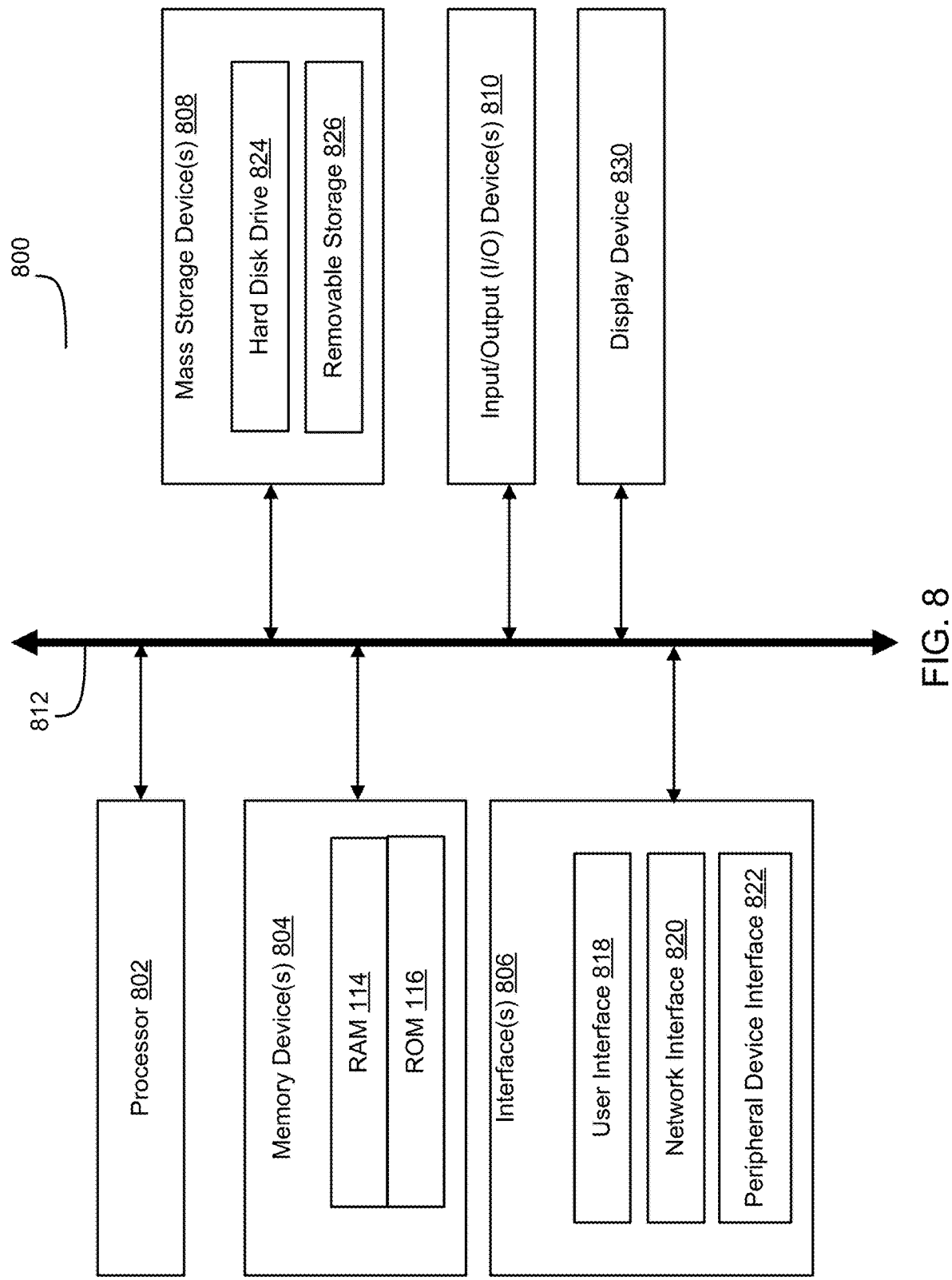
FIG. 8 illustrates an embodiment of hardware in accordance with the principles and teachings of the disclosure.

As can be seen in FIG. 8, various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

FIG. 8 is a block diagram illustrating an example computing device 800. Computing device 800 may be used to perform various procedures, such as those discussed herein. Computing device 800 can function as a server, a client, or any other computing entity. Computing device can perform various monitoring functions as discussed herein, and can execute one or more application programs, such as the application programs described herein. Computing device 800 can be any of a wide variety of computing devices, such as a desktop computer, a notebook computer, a server computer, a handheld computer, camera control unit, tablet computer and the like.

Computing device 800 includes one or more processor(s) 802, one or more memory device(s) 804, one or more interface(s) 806, one or more mass storage device(s) 808, one or more Input/Output (I/O) device(s) 810, and a display device 830 all of which are coupled to a bus 812. Processor(s) 802 include one or more processors or controllers that execute instructions stored in memory device(s) 804 and/or mass storage device(s) 808. Processor(s) 802 may also include various types of computer-readable media, such as cache memory.

Memory device(s) 804 include various computer-readable media, such as volatile memory (e.g., random access memory (RAM) 814) and/or nonvolatile memory (e.g., read-only memory (ROM) 816). Memory device(s) 804 may also include rewritable ROM, such as Flash memory.

Mass storage device(s) 808 include various computer readable media, such as magnetic tapes, magnetic disks, optical disks, solid-state memory (e.g., Flash memory), and so forth. As shown in FIG. 8, a particular mass storage device is a hard disk drive 824. Various drives may also be included in mass storage device(s) 808 to enable reading from and/or writing to the various computer readable media. Mass storage device(s) 808 include removable media 826 and/or non-removable media.

I/O device(s) 810 include various devices that allow data and/or other information to be input to or retrieved from computing device 800. Example I/O device(s) 810 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 830 includes any type of device capable of displaying information to one or more users of computing device 800. Examples of display device 830 include a monitor, display terminal, video projection device, and the like.

Interface(s) 806 include various interfaces that allow computing device 800 to interact with other systems, devices, or computing environments. Example interface(s) 806 may include any number of different network interfaces 820, such as interfaces to local area networks (LANs), wide area networks (WANs), wireless networks, and the Internet. Other interface(s) include user interface 818 and peripheral device interface 822. The interface(s) 806 may also include one or more user interface elements 818. The interface(s) 806 may also include one or more peripheral interfaces such as interfaces for printers, pointing devices (mice, track pad, etc.), keyboards, and the like.

Bus 812 allows processor(s) 802, memory device(s) 804, interface(s) 806, mass storage device(s) 808, and I/O device(s) 810 to communicate with one another, as well as other devices or components coupled to bus 812. Bus 812 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 800, and are executed by processor(s) 802. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Figure 9A:
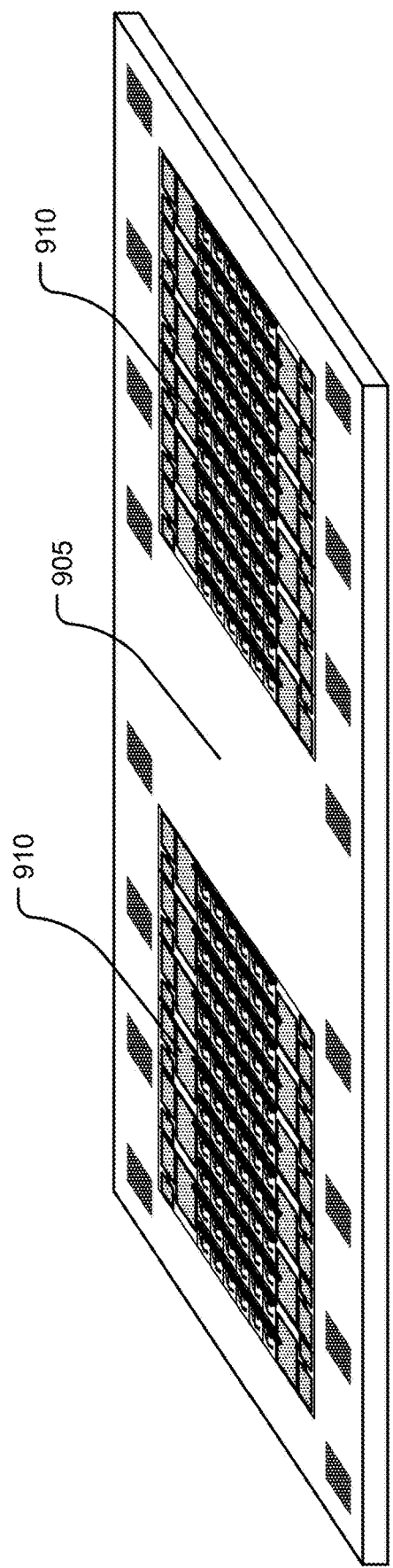
FIGS. 9A and 9B illustrate views of an implementation of an imaging sensor having a plurality of pixel arrays for producing a three dimensional image in accordance with the teachings and principles of the disclosure.
Figure 9B:
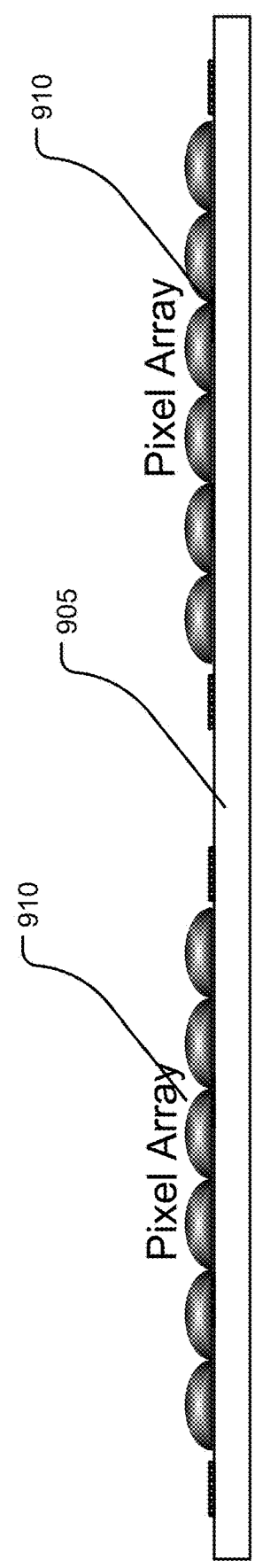

FIGS. 9A and 9B illustrate an implementation of a monolithic sensor 905 having a plurality of pixel arrays 910 for producing a three dimensional image in accordance with the teachings and principles of the disclosure. Such an implementation may be desirable for three dimensional image capture, wherein the two pixel arrays 910 may be offset during use. In another implementation, a first pixel array 910 and a second pixel array 910 may be dedicated to receiving a predetermined range of wave lengths of electromagnetic radiation, wherein the first pixel array 910 is dedicated to a different range of wave length electromagnetic radiation than the second pixel array 910.

Figure 10A:
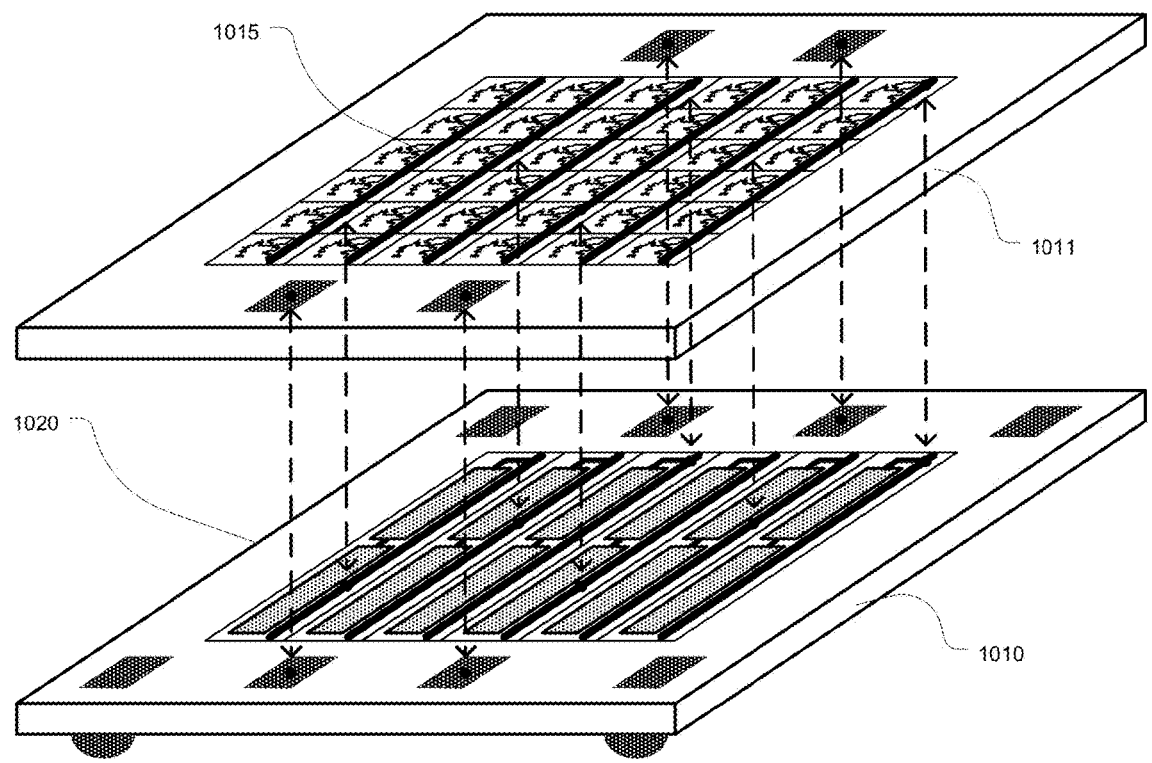
FIGS. 10A and 10B illustrate views of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 10B:
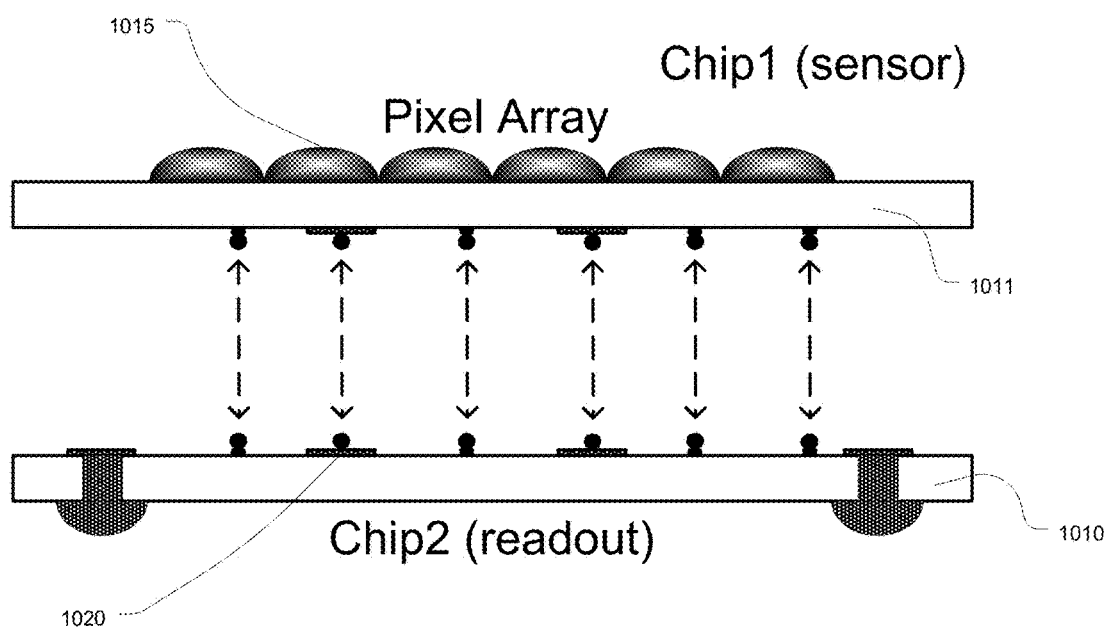

FIGS. 10A and 10B illustrate a perspective view of an implementation of an imaging sensor built on a plurality of substrates 1010, 1011. As illustrated, a plurality of pixel columns forming the pixel array 1015 are located on the first substrate 1011 and a plurality of circuit columns 1020 are located on a second substrate 1010. Also illustrated in the figure are the electrical connection and communication between one column of pixels to its associated or corresponding column of circuitry.

In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first of the two substrates/chips may be processed using an image CMOS process. The first substrate/chip may be comprised either of a pixel array exclusively or a pixel array surrounded by limited circuitry. The second or subsequent substrate/chip may be processed using any process, and does not have to be from an image CMOS process. The second substrate/chip may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip may be stacked with the second or subsequent substrate/chip using any three-dimensional technique. The second substrate/chip may support most, or a majority, of the circuitry that would have otherwise been implemented in the first image CMOS chip (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wirebonds, bump and/or TSV (Through Silicon Via).

FIGS. 11A and 11B illustrate a perspective view of an implementation of an imaging sensor having a plurality of pixel arrays for producing a three dimensional image. The three dimensional image sensor may be built on a plurality of substrates 1111a, 1111b, 1111c, and may comprise the plurality of pixel arrays 1115a, 1115b and other associated circuitry 1130a, 1130b, wherein a plurality of pixel columns forming the first pixel array and a plurality of pixel columns forming a second pixel array are located on respective substrates and a plurality of circuit columns are located on a separate substrate. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

It will be appreciated that various features disclosed herein provide significant advantages and advancements in the art. The following embodiments are exemplary of some of those features.

In the foregoing Detailed Description of the Disclosure, various features of the disclosure are grouped together in a single embodiment for the purpose of streamlining the disclosure. This method of disclosure is not to be interpreted as reflecting an intention that the claimed disclosure requires more features than are expressly recited in each claim. Rather, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and Claims to refer to particular system components. As one skilled in the art will appreciate, components may be referred to by different names. This document does not intend to distinguish between components that differ in name, but not function.

What is claimed is:

1. An endoscopic device comprising:
a CMOS image sensor being disposed near a tip of a distal end of the endoscopic device;
a plurality of on-chip registers integrated into the CMOS image sensor for configuring the image sensor operation; and
a plurality of bidirectional pads directly connected to the CMOS image sensor which all operate as pads to input and output digital data from the CMOS image sensor such that the number of pads necessary to exchange the input and output of digital data in the CMOS image sensor is reduced by combining digital input and output functionality into the same bi-directional pads;
wherein the image sensor is configured to control each of the plurality of bidirectional pads to have an output state and an input state;
wherein the image sensor automatically switches between the output state and the input state for the plurality of bidirectional pads;
wherein when the plurality of bidirectional pads are in the output state pixel data generated by exposing one or more pixels within the image sensor is output from the image sensor through each one of the bidirectional pads within the plurality of bidirectional pads and wherein when the plurality of bidirectional pads are in the input state each one of the plurality of bidirectional pads receive control commands for the operation of the image sensor which are communicated to the on-chip registers through connections between the plurality of bidirectional pads and the CMOS image sensor; and
wherein the CMOS image sensor is the only digital device that is disposed near the tip of the distal end of the endoscopic device.

2. The endoscopic device of claim 1, further comprising a state identifier that identifies what state the bidirectional pads are in during a frame period.

3. The endoscopic device of claim 1, wherein the endoscopic device does not issue slow-control commands into the bidirectional pads during the output state.

4. The endoscopic device of claim 1, further comprising an emitter which illuminates a scene, wherein pulse control for the emitter corresponds to the bidirectional pad state.

5. The endoscopic device of claim 4, wherein a pulse is emitted by the emitter during the configuration state.

6. The endoscopic device of claim 4, wherein a pulse of light is emitted by the emitter.

7. The endoscopic device of claim 4, wherein a pulse of light is emitted by the emitter during the input state.

8. An endoscopic system comprising:
an image sensor disposed near a tip of a distal end of a lumen of the endoscope;
a plurality of on-chip registers integrated into the image sensor for configuring the image sensor operation; and
a plurality of bidirectional pads directly connected to the CMOS image sensor which all operate as pads to input and output digital data from the CMOS image sensor such that the number of pads necessary to exchange the input and output of digital data in the CMOS image sensor is reduced by combining digital input and output functionality into the same bi-directional pads;
wherein the endoscopic system controls each of the plurality of bidirectional pads to have an output state and an input state;
wherein the endoscopic system automatically switches between the output state and the input state for the plurality of bidirectional pads,
wherein when the plurality of bidirectional pads are in the output state pixel data generated by exposing one or more pixels within the image sensor is output from the image sensor through each one of the bidirectional pads within the plurality of bidirectional pads and wherein when the plurality of bidirectional pads are in the input state each one of the plurality of bidirectional pads receive control commands for the operation of the image sensor which are communicated to the on-chip registers through connections between the plurality of bidirectional pads and the image sensor; and
wherein the image sensor is the only digital device that is disposed near the tip of the distal end of the endoscopic device.

9. The endoscopic system of claim 8, wherein the endoscopic system uses a serial command protocol to electronically communicate with the sensor when the plurality of bidirectional pads are in the input state.

10. The endoscopic system of claim 8, further comprising a clock for coordinating a function of external devices in electronic communication with the endoscopic system.

11. The endoscopic system of claim 8, wherein the image sensor is a minimal area image sensor for use at a distal end of the endoscope.

12. The endoscopic system of claim 11, further comprising a voltage converter to provide power to at least the image sensor circuitry from an external power supply source.

13. The endoscopic system of claim 8, further comprising a plurality of voltage converters integrated into the image sensor chip to provide for multiple internal voltage supply levels based in a single power level input.

14. The endoscopic system of claim 13, wherein the voltage converters comprise an up converter.

15. The endoscopic system of claim 13, wherein the voltage converters comprise a down converter.

16. The endoscopic system of claim 8, further comprising a single data line to each of the plurality of bidirectional pads.

17. The endoscopic system of claim 8, further comprising connections between a plurality of data lines to a sensor.

18. The endoscopic system of claim 13, wherein the converter is a switch-cap DC-DC converter.

19. The endoscopic system of claim 13, wherein the converter is a LDO converter.

20. The endoscopic system of claim 13, wherein the converter is a switch-cap DC-DC converter and a LDO converter.

21. The endoscopic system of claim 8, wherein the endoscopic system provides analog data to the image sensor, wherein the image sensor comprises an analog to digital converter to receive and convert external device data.

22. The endoscopic system of claim 8, wherein the endoscopic system uses serial protocol to transmit digital data to the image sensor.

23. The endoscopic system of claim 8, further comprising a user interface having a button that may be pressed by an operator to aid in the operation of the endoscope.

24. The endoscopic system of claim 8, further comprising an angle sensor to determine an angle of an endoscope lumen relative a hand-piece.

25. The endoscopic system of claim 24, wherein the angle sensor is of Hall Effect type.

26. The endoscopic system of claim 24, wherein the angle sensor is of potentiometer type.

27. The endoscopic system of claim 24, wherein the angle sensor is of optoelectronic type.

28. The endoscopic system of claim 8, further comprising a state identifier that identifies what state the bidirectional pads are in during an operation cycle over the system.

29. The endoscopic system of claim 8, wherein the endoscopic system does not issue slow-control commands during the output state.

30. The endoscopic system of claim 8, further comprising an emitter wherein light pulse control corresponds to the bidirectional pad state.

31. The endoscopic system of claim 30, wherein a light pulse is emitted by the emitter.

32. The endoscopic system of claim 30, wherein a light pulse is emitted during the input state.

33. The endoscopic system of claim 30, wherein a light pulse is emitted at a particular color wavelength.

* * * * *